United States Patent [19]
Cuny et al.

[11] Patent Number: 5,772,673
[45] Date of Patent: Jun. 30, 1998

[54] APPARATUS FOR APPLYING SURGICAL CLIPS

[75] Inventors: Douglas J. Cuny, Bethel; Ernie Aranyi, Easton; Scott W. Reed, Shelton; Vinod C. Nagori, Trumbull, all of Conn.

[73] Assignee: United States Surgical Corporation, Norwalk, Conn.

[21] Appl. No.: 611,962

[22] Filed: Mar. 7, 1996

[51] Int. Cl.[6] ................................................. A61B 17/10
[52] U.S. Cl. ........................ 606/142; 606/143; 606/144; 227/901
[58] Field of Search ..................................... 606/142, 139, 606/143, 129, 151, 157, 158; 227/901, 175.1; 222/902, 175.2, 175.3, 176.1, 177.1, 180.1, 181.1, 182.1

[56] References Cited

U.S. PATENT DOCUMENTS

| | | |
|---|---|---|
| 2,968,041 | 1/1961 | Skold . |
| 3,777,538 | 12/1973 | Weatherly et al. . |
| 4,027,510 | 6/1977 | Hiltebrandt . |
| 4,084,594 | 4/1978 | Mosior . |
| 4,152,920 | 5/1979 | Green . |
| 4,166,466 | 9/1979 | Jarvik . |
| 4,226,242 | 10/1980 | Jarvik . |
| 4,242,902 | 1/1981 | Green . |
| 4,296,751 | 10/1981 | Blake, III et al. . |
| 4,316,468 | 2/1982 | Klieman et al. . |
| 4,425,915 | 1/1984 | Ivanov . |
| 4,430,997 | 2/1984 | DiGiovanni et al. . |
| 4,509,518 | 4/1985 | McGarry et al. . |
| 4,534,351 | 8/1985 | Rothfuss et al. . |
| 4,562,839 | 1/1986 | Blake, III et al. . |
| 4,576,166 | 3/1986 | Montgomery et al. . |
| 4,598,711 | 7/1986 | Deniega . |
| 4,646,740 | 3/1987 | Peters et al. . |
| 4,712,549 | 12/1987 | Peters et al. . |
| 4,850,355 | 7/1989 | Brooks et al. . |
| 5,030,226 | 7/1991 | Green et al. . |
| 5,049,152 | 9/1991 | Simon et al. . |
| 5,084,057 | 1/1992 | Green et al. . |
| 5,100,420 | 3/1992 | Green et al. . |
| 5,104,395 | 4/1992 | Thornton et al. . |
| 5,112,343 | 5/1992 | Thornton . |
| 5,171,247 | 12/1992 | Hughett et al. . |
| 5,171,249 | 12/1992 | Stefanchik et al. . |
| 5,527,320 | 6/1996 | Carruthers et al. ................. 606/143 |

FOREIGN PATENT DOCUMENTS

| | | |
|---|---|---|
| 0605254 | 7/1994 | European Pat. Off. . |
| 0612505 | 8/1994 | European Pat. Off. . |
| 0671148 | 9/1995 | European Pat. Off. . |
| 0680729 | 11/1995 | European Pat. Off. . |
| 94132968 | 11/1994 | Germany . |
| 4434864 | 4/1996 | Germany . |

*Primary Examiner*—Michael Buiz
*Assistant Examiner*—Tina T. D. Pham

[57] ABSTRACT

An apparatus for application of surgical clips to body tissue is disclosed having a handle assembly and an elongated body portion extending distally from the handle assembly. A jaw assembly is mounted at a distal end portion of the elongated body portion and includes first and second jaws movable between an open position and a closed position. An actuator is disclosed which is slidable within the elongated body portion in response to actuation of the handle assembly. The actuator has camming structure at a distal portion thereof for moving the first and second jaws between the open position and the closed position. A loading unit is releasably mounted to the elongated body portion and stores a plurality of surgical clips therein. The loading unit includes a clip advancer having a portion engageable with the actuator and movable therewith for advancing a distalmost surgical clip and a ratchet assembly associated with the clip advancer to index progressive movement thereof.

23 Claims, 28 Drawing Sheets

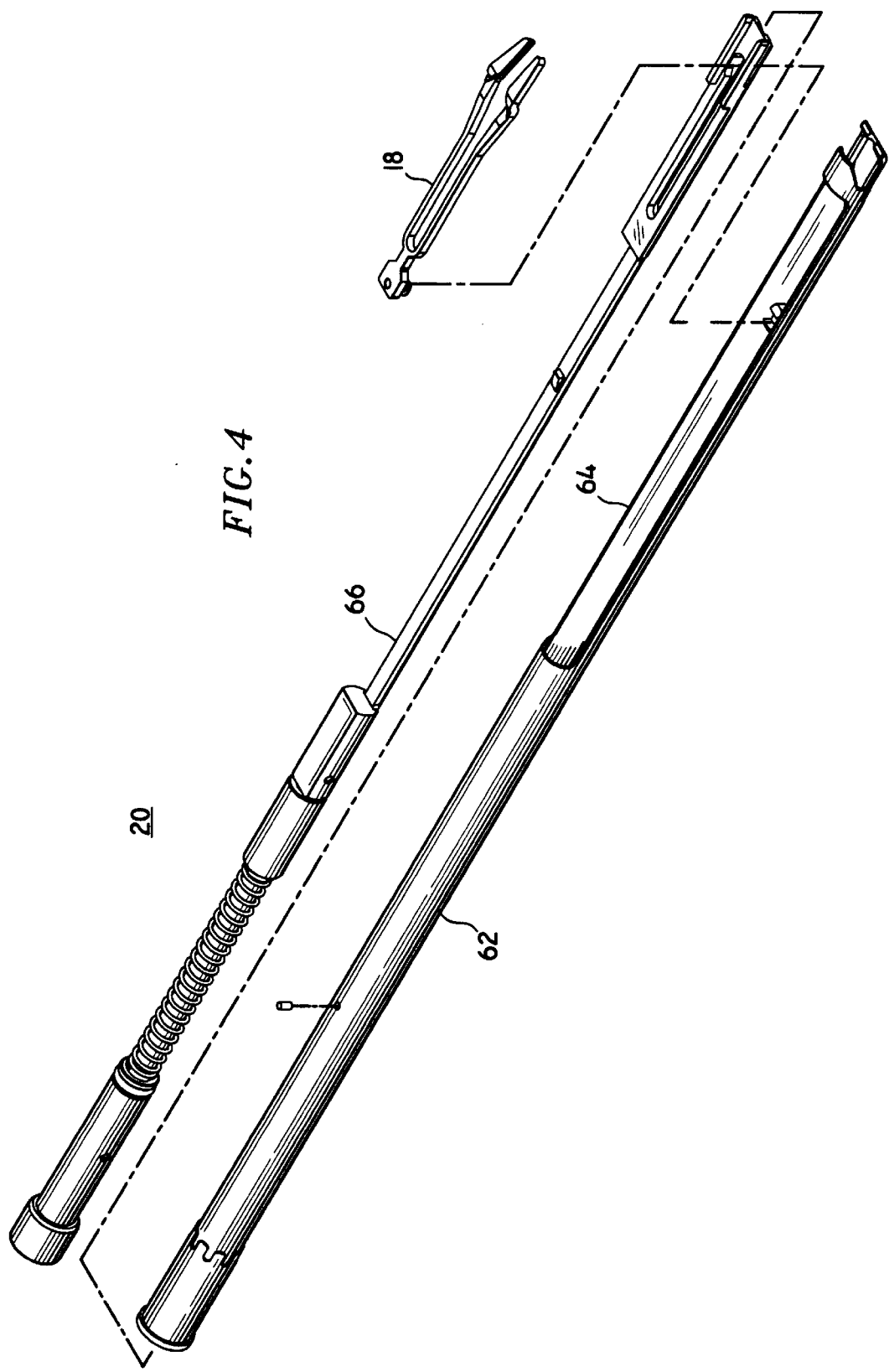

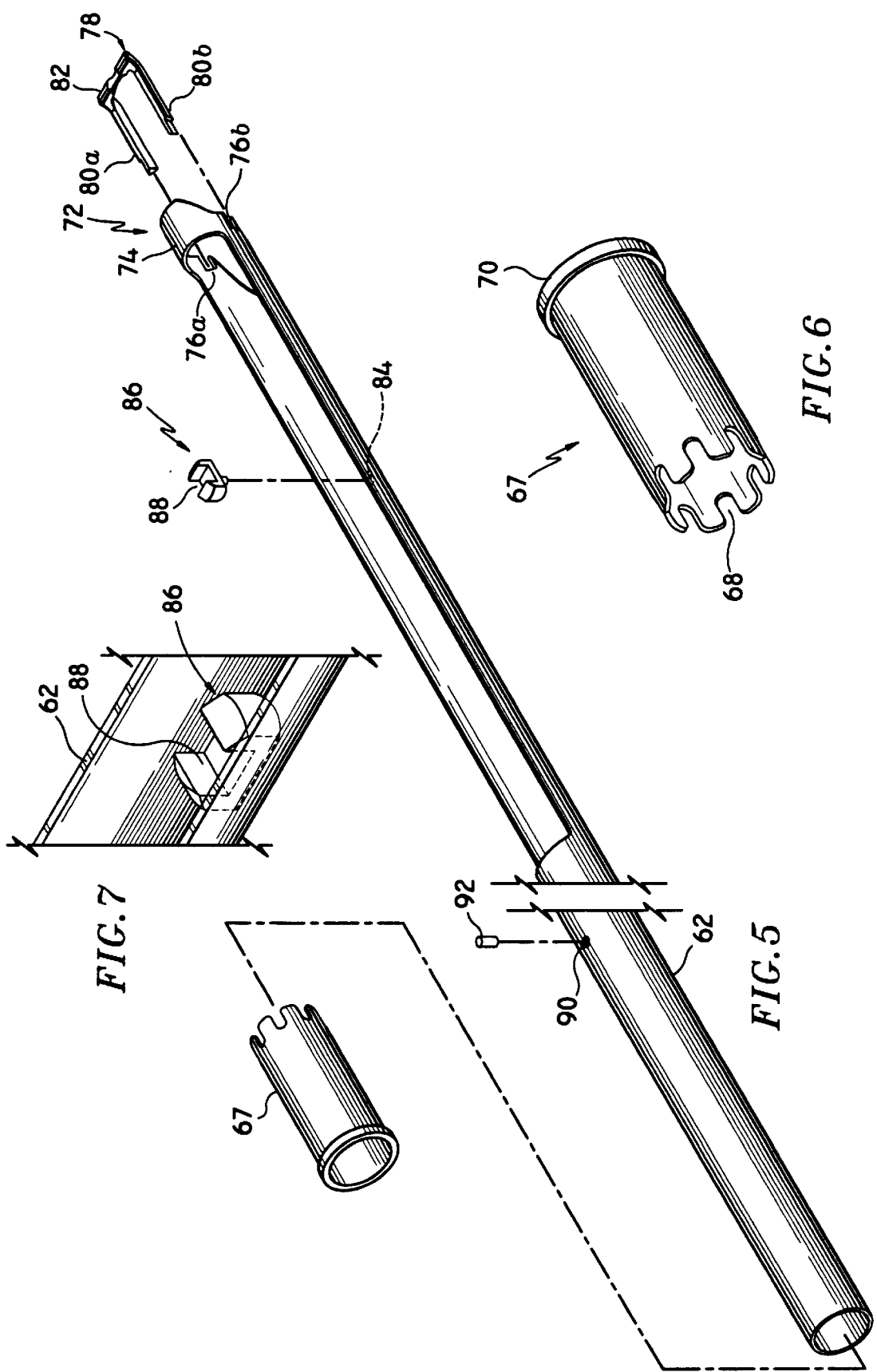

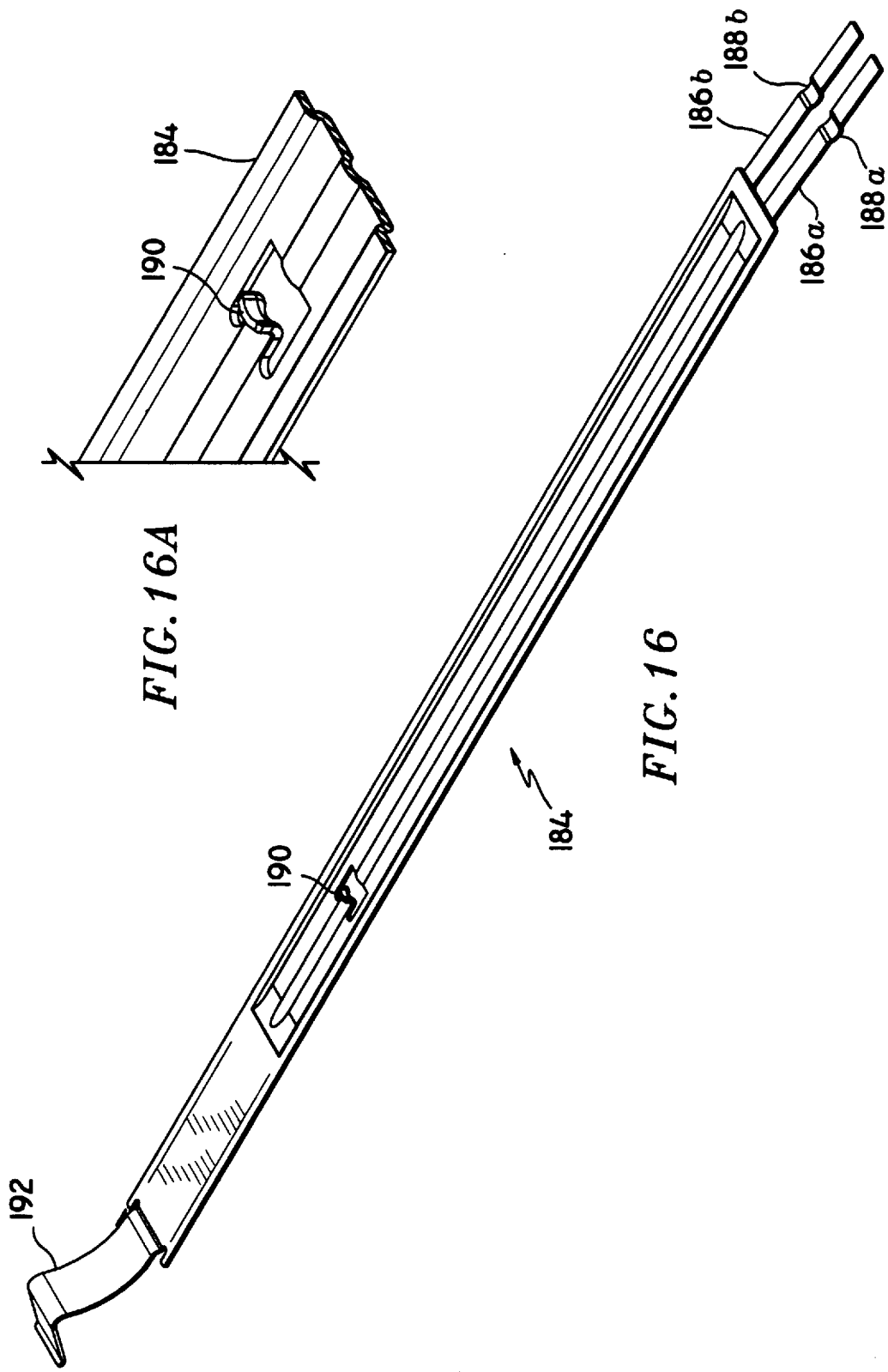

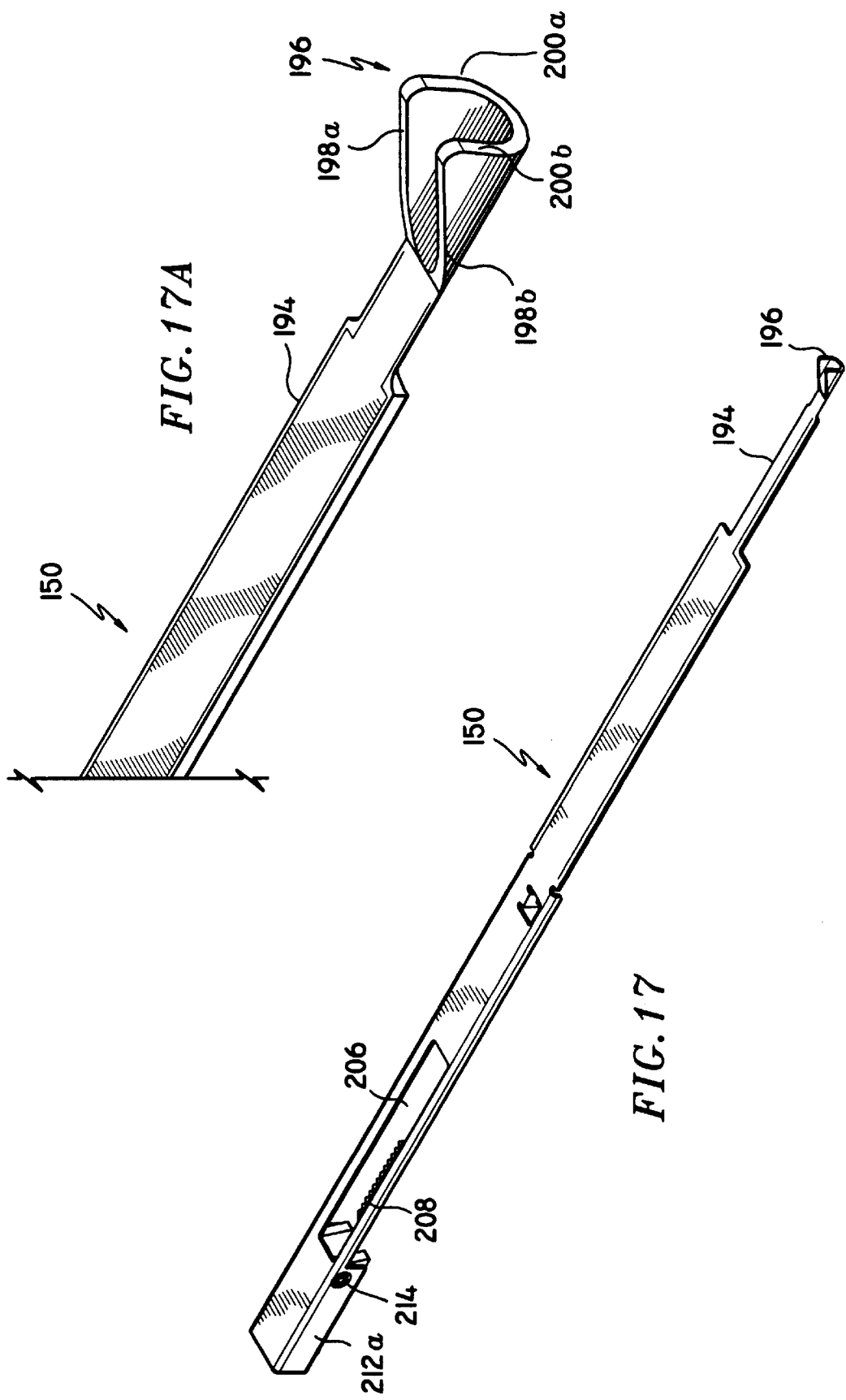

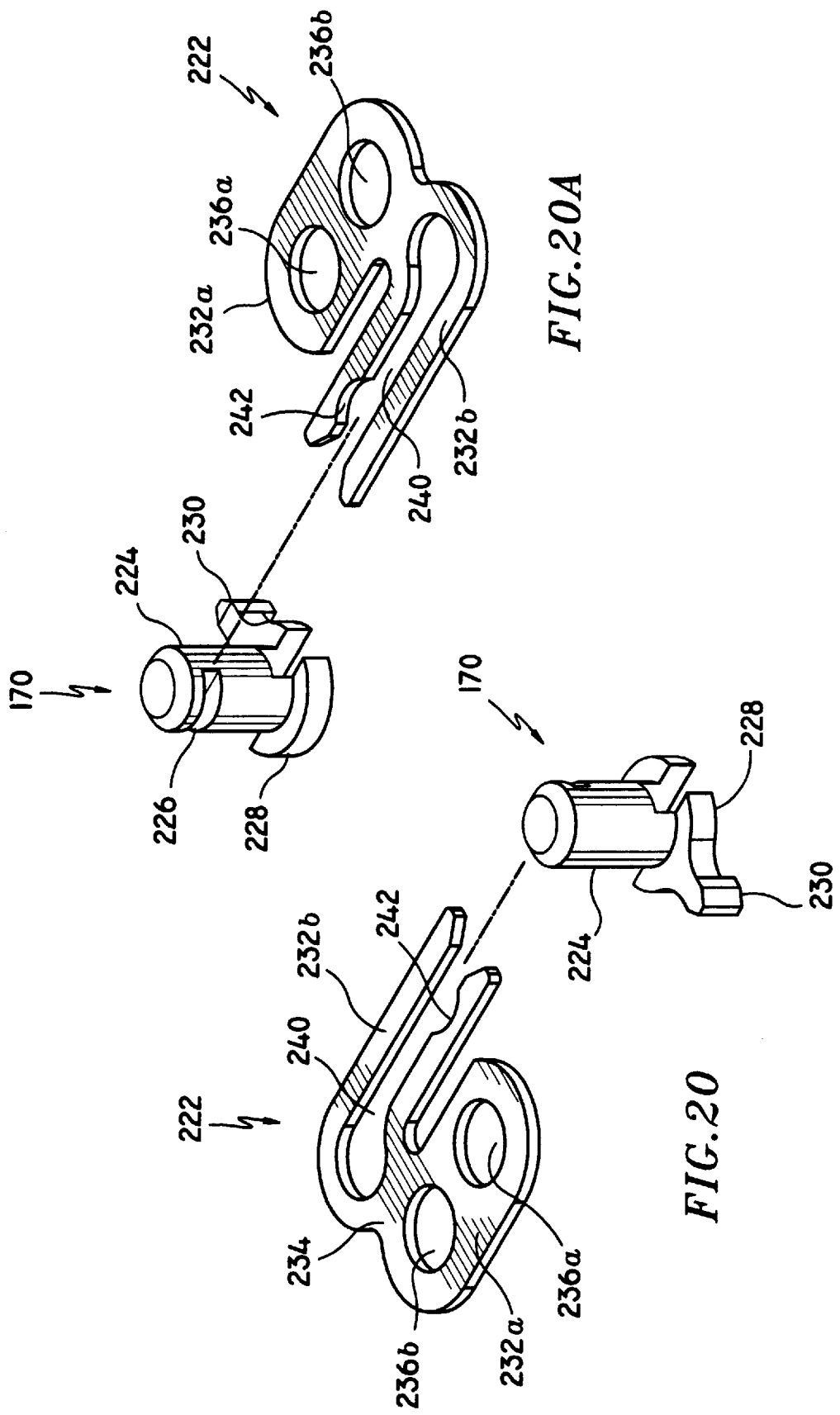

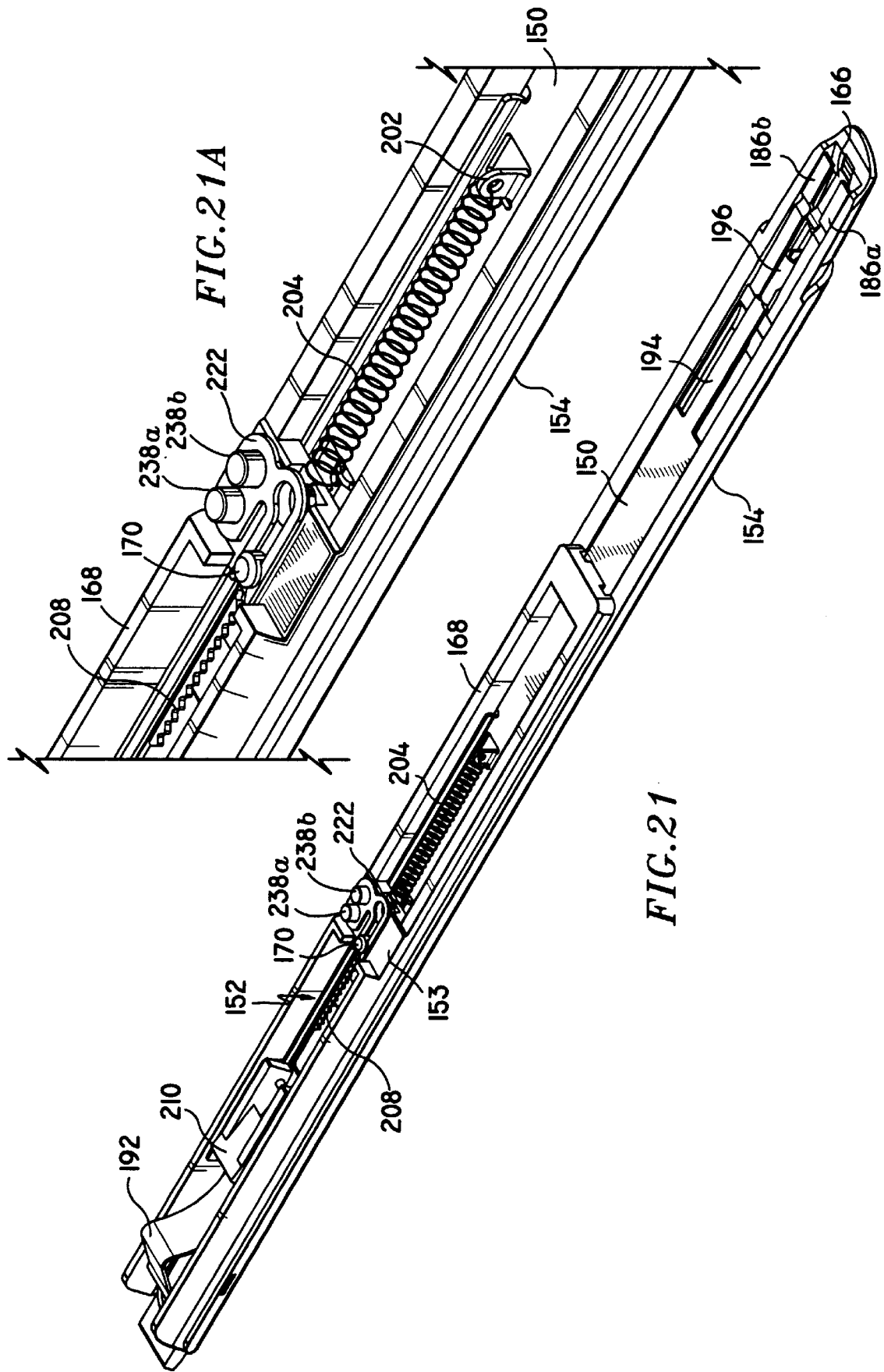

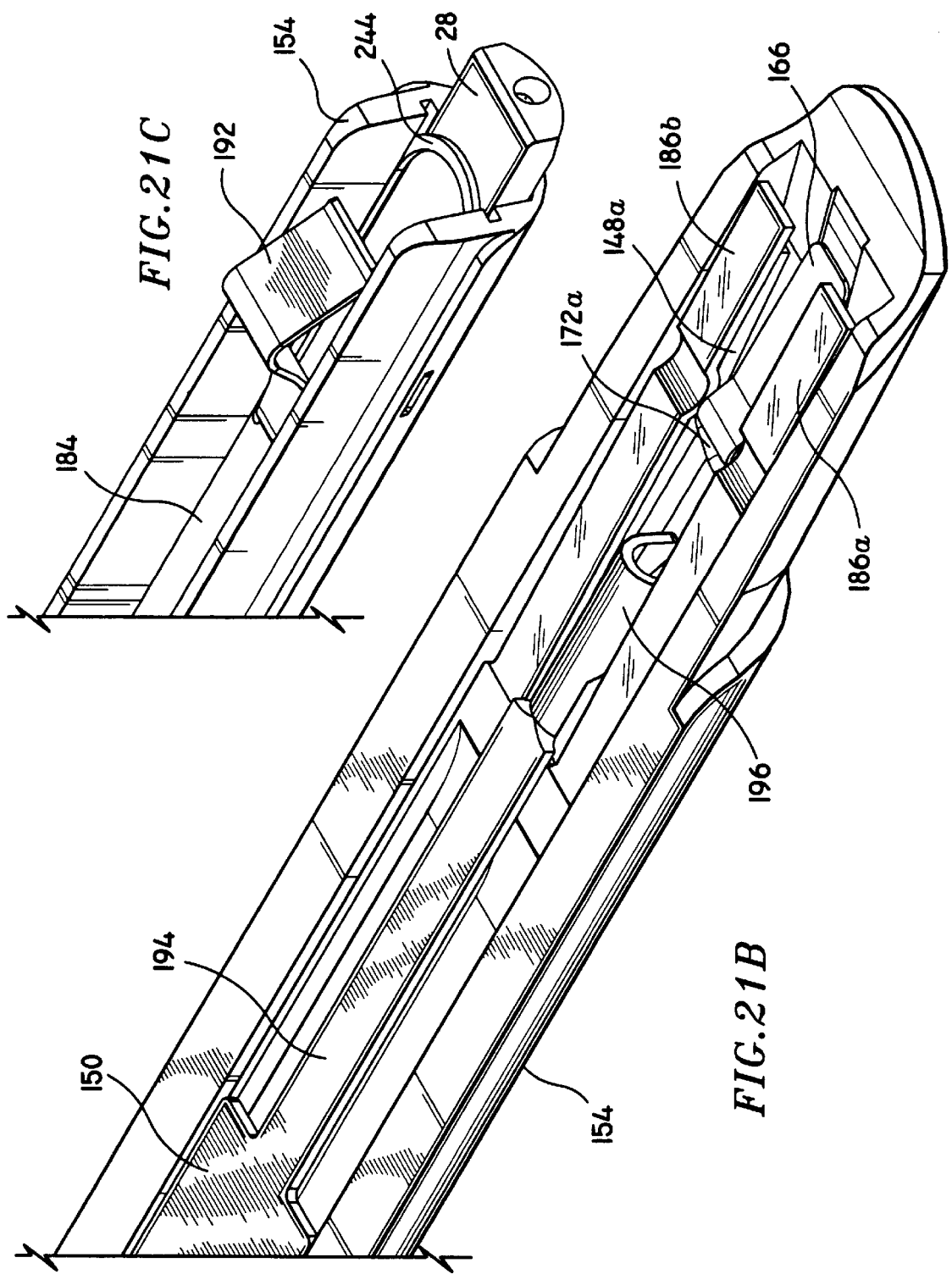

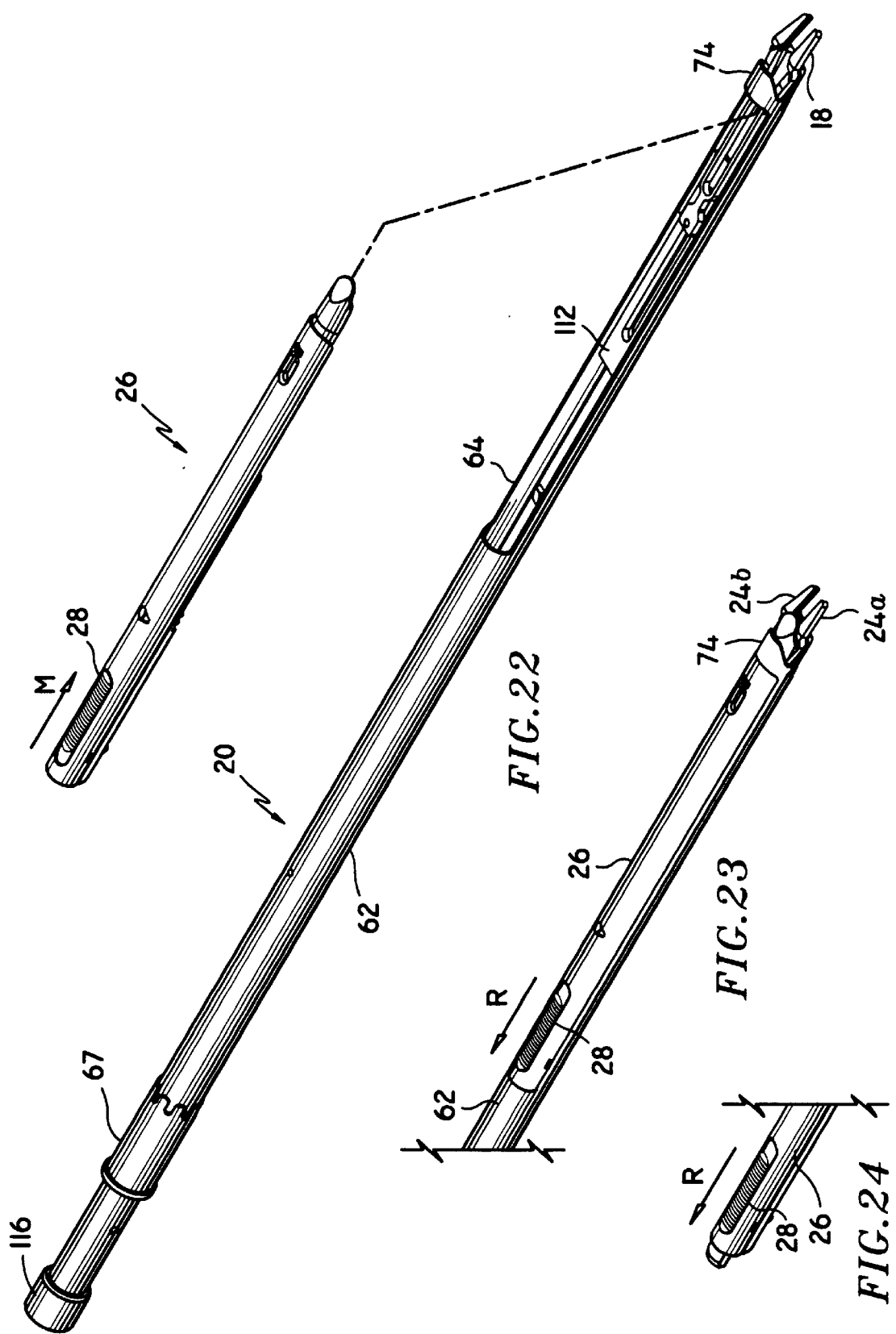

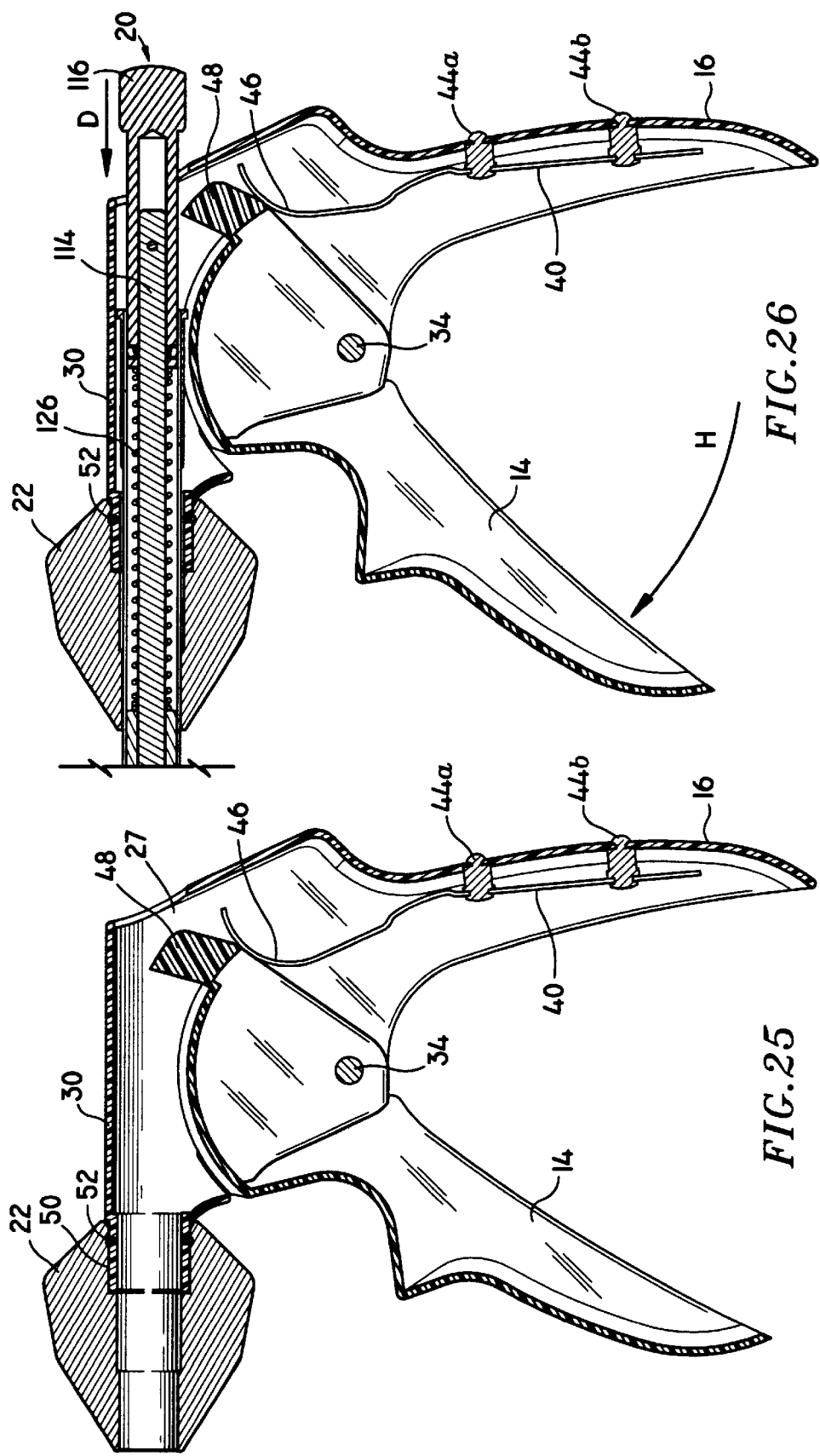

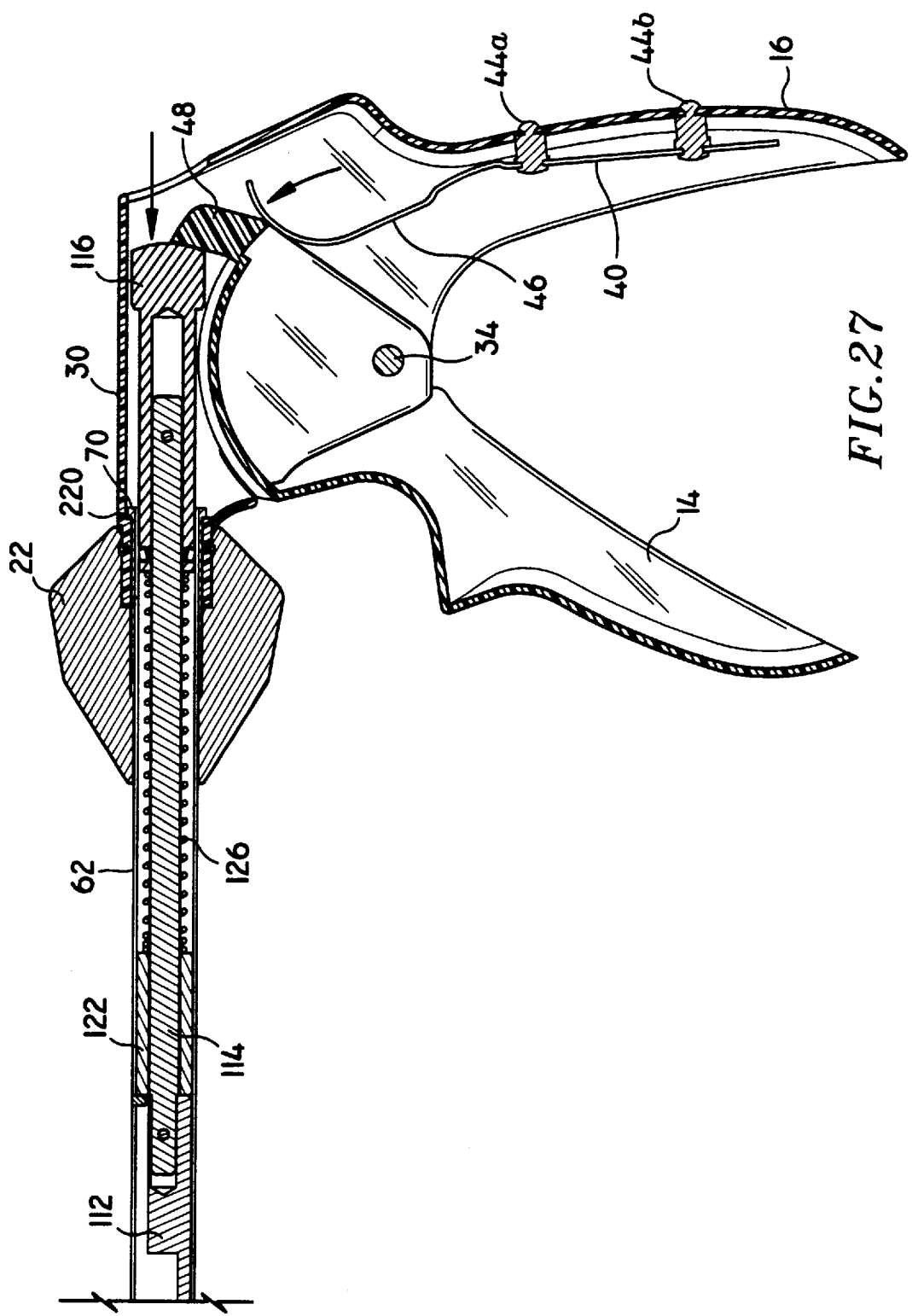

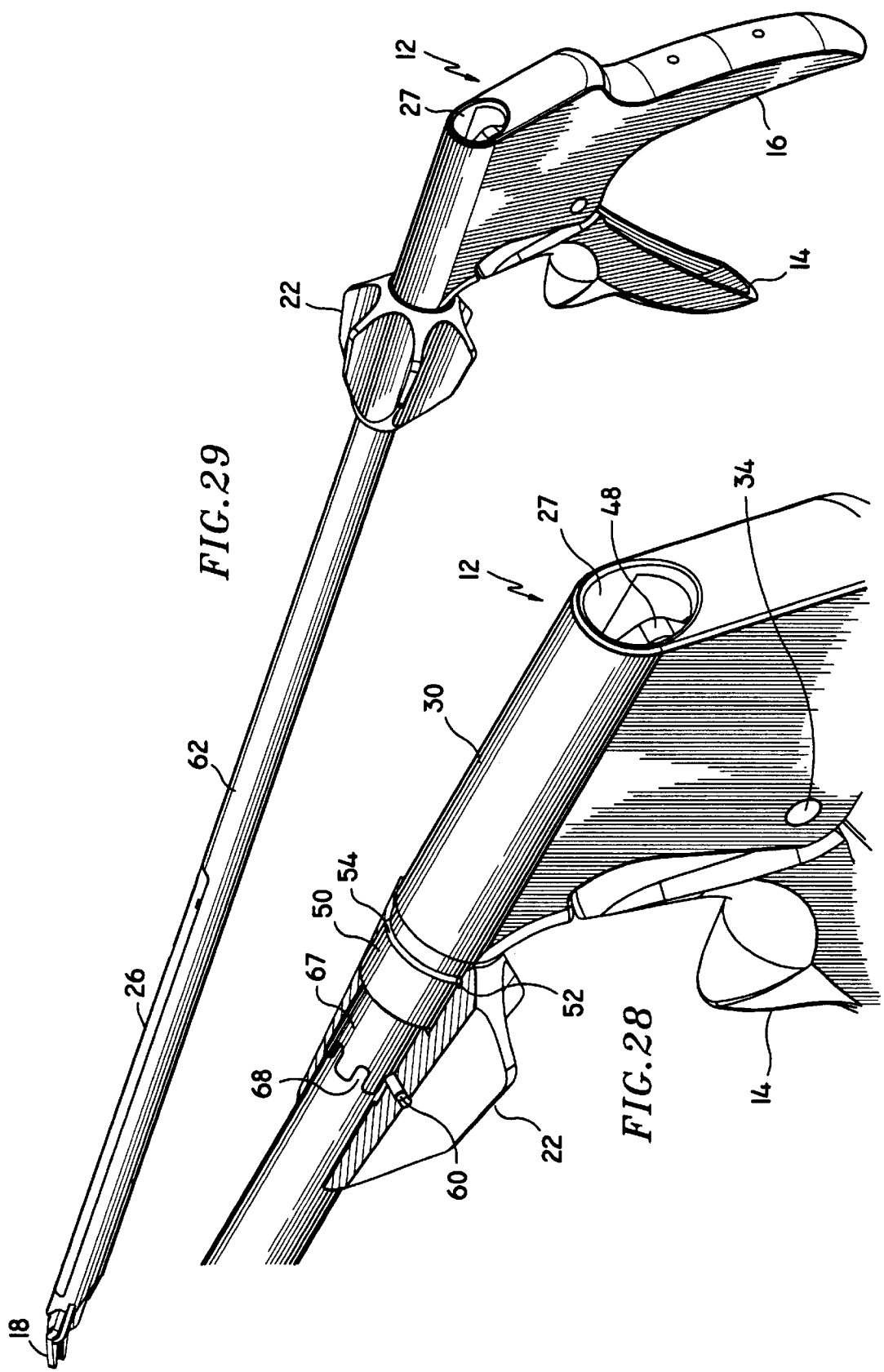

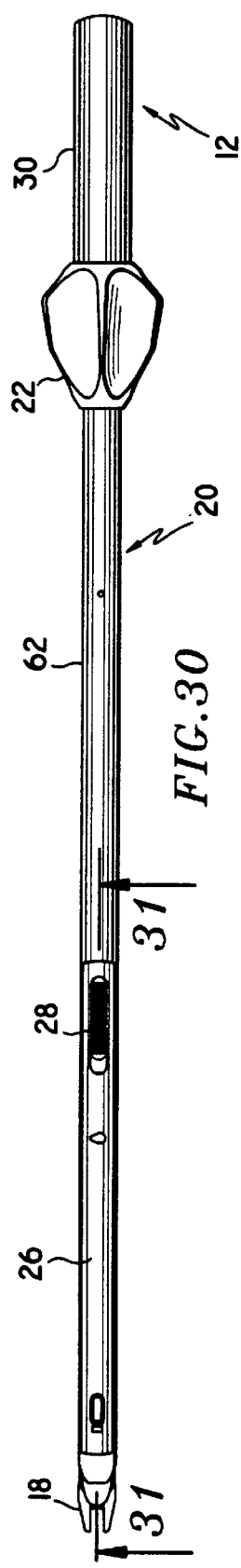
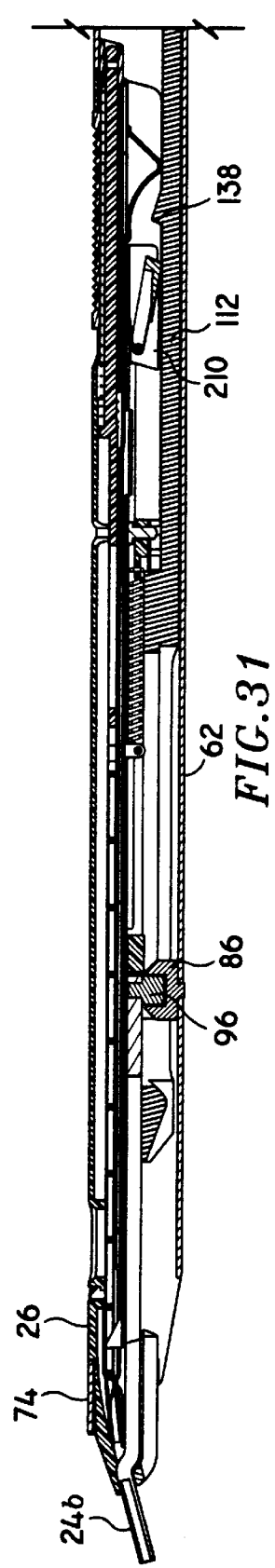
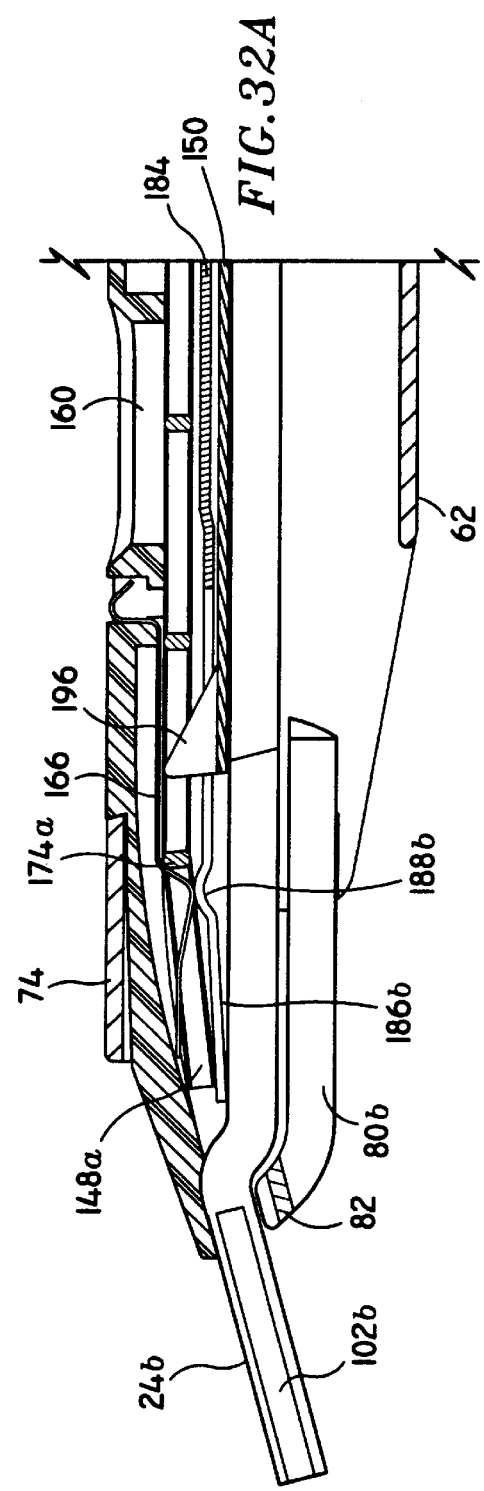

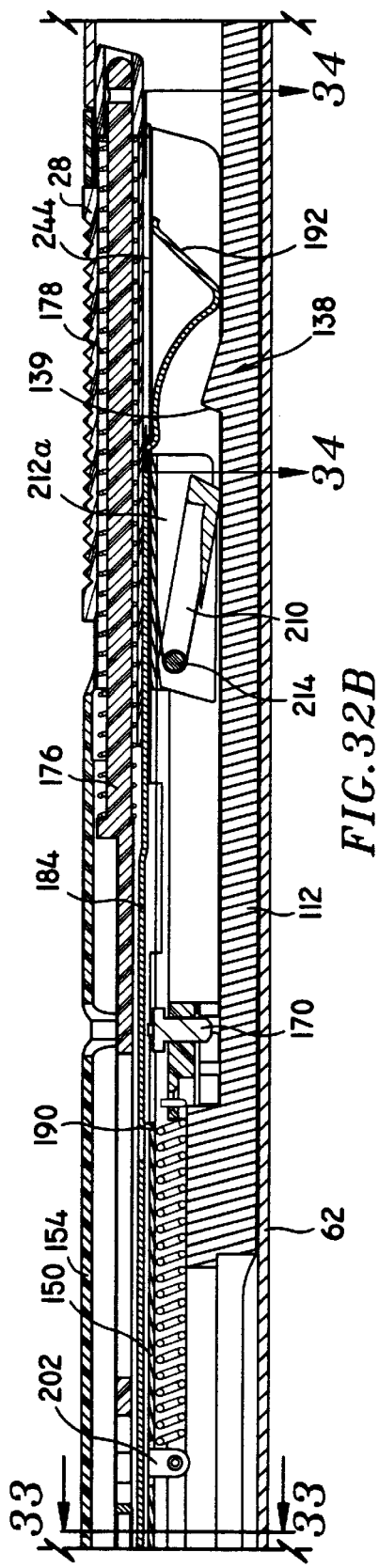
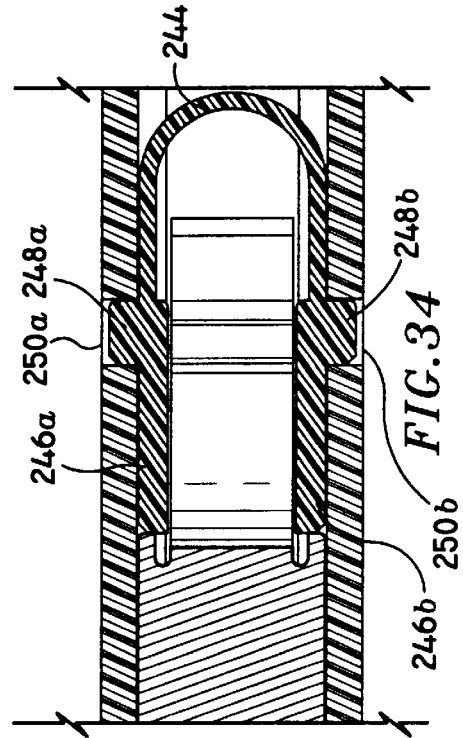
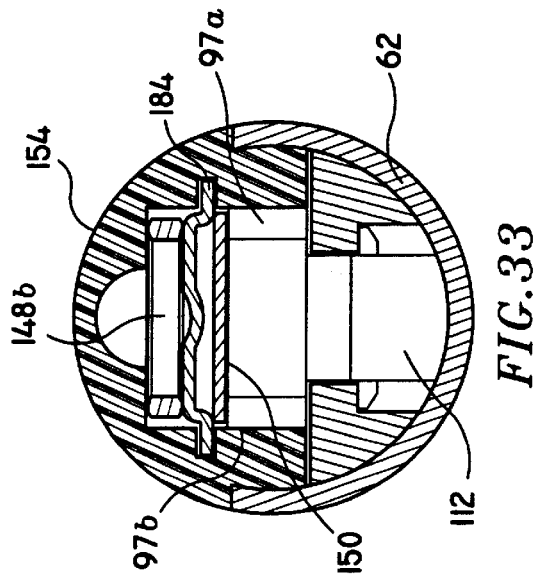

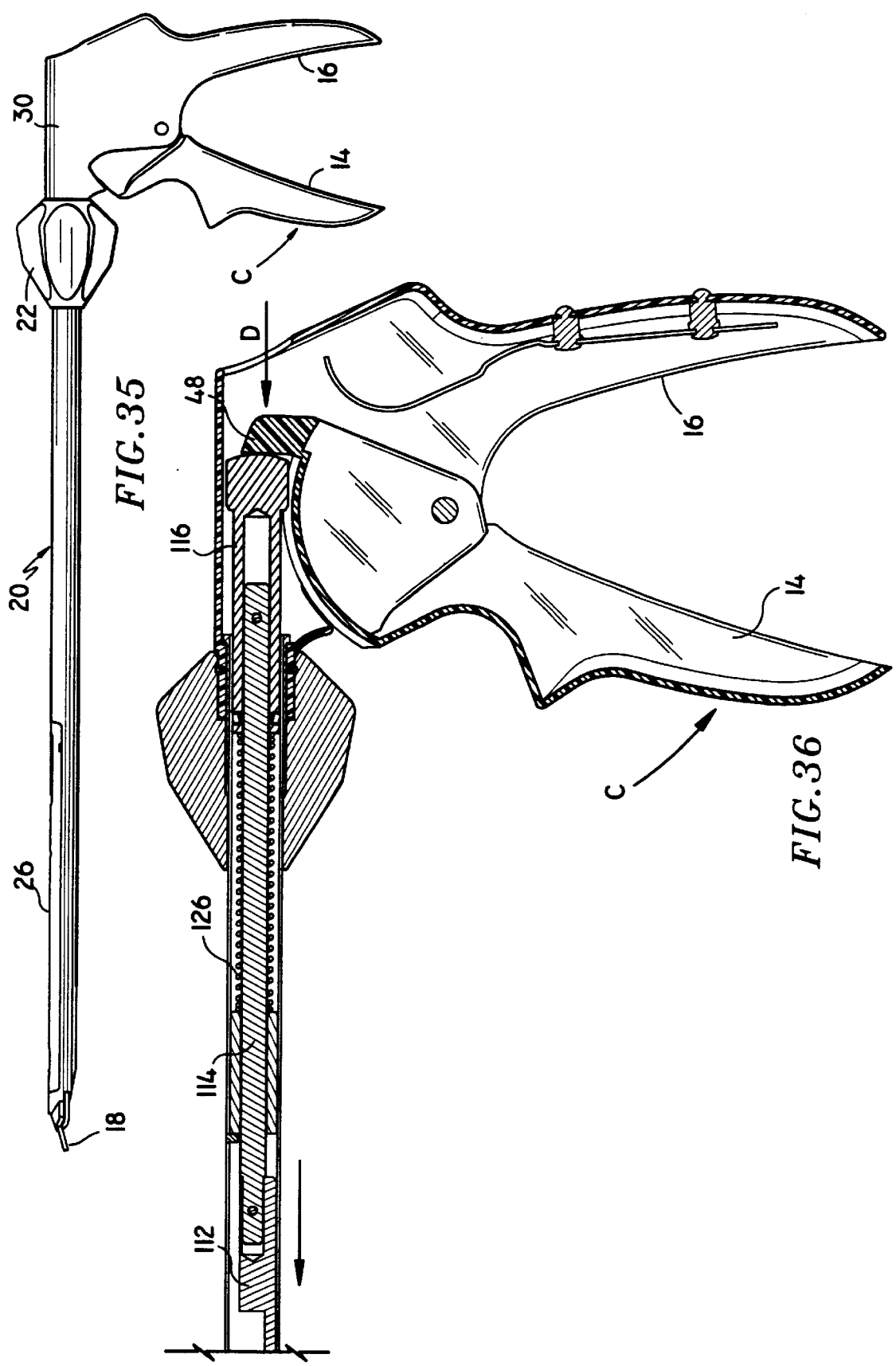

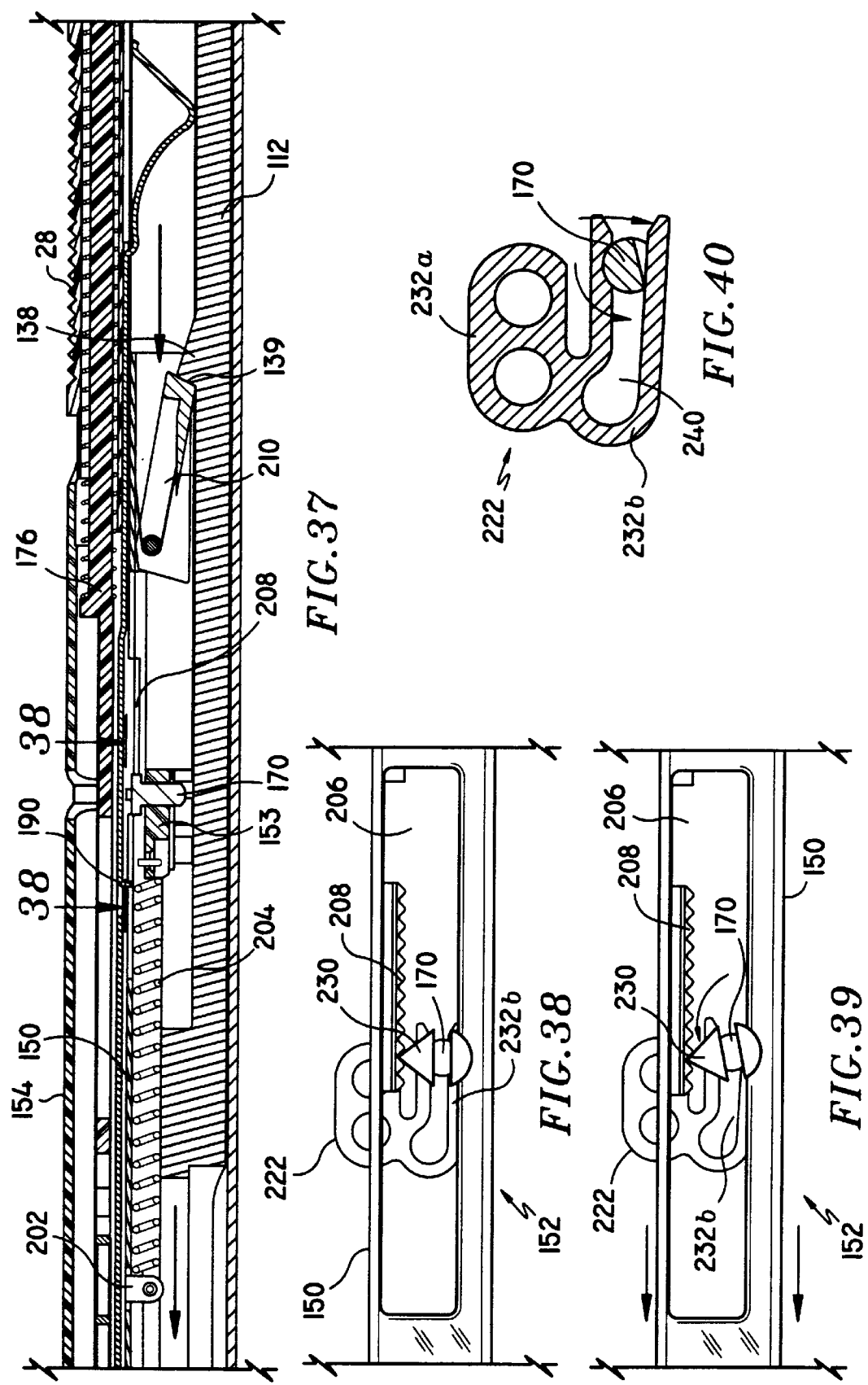

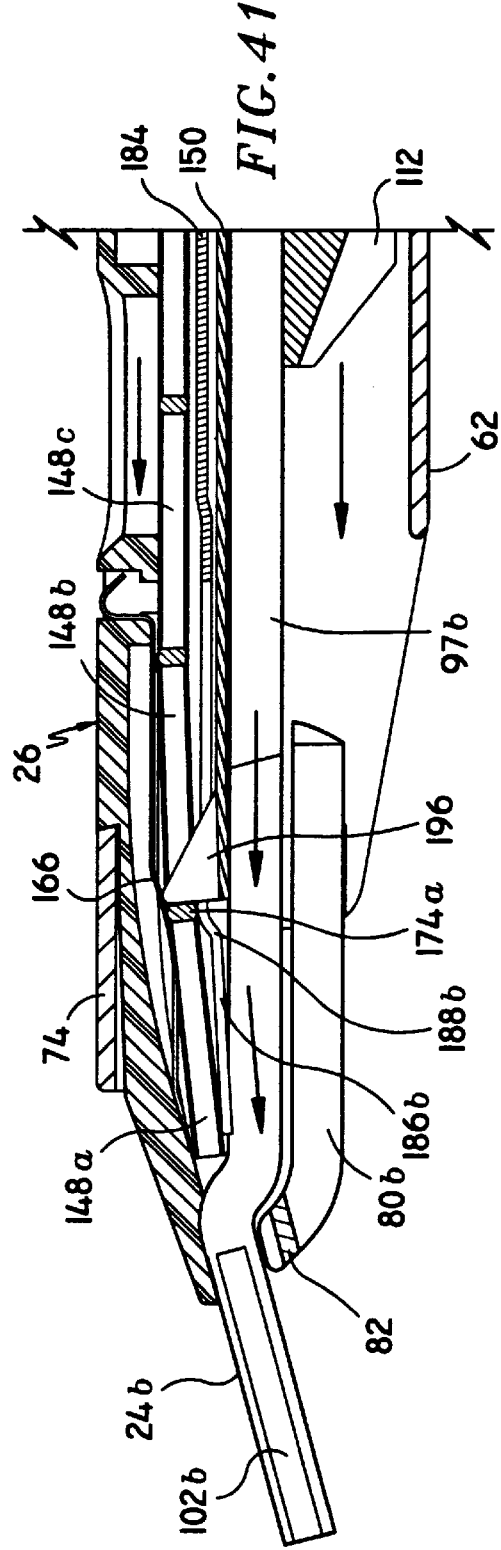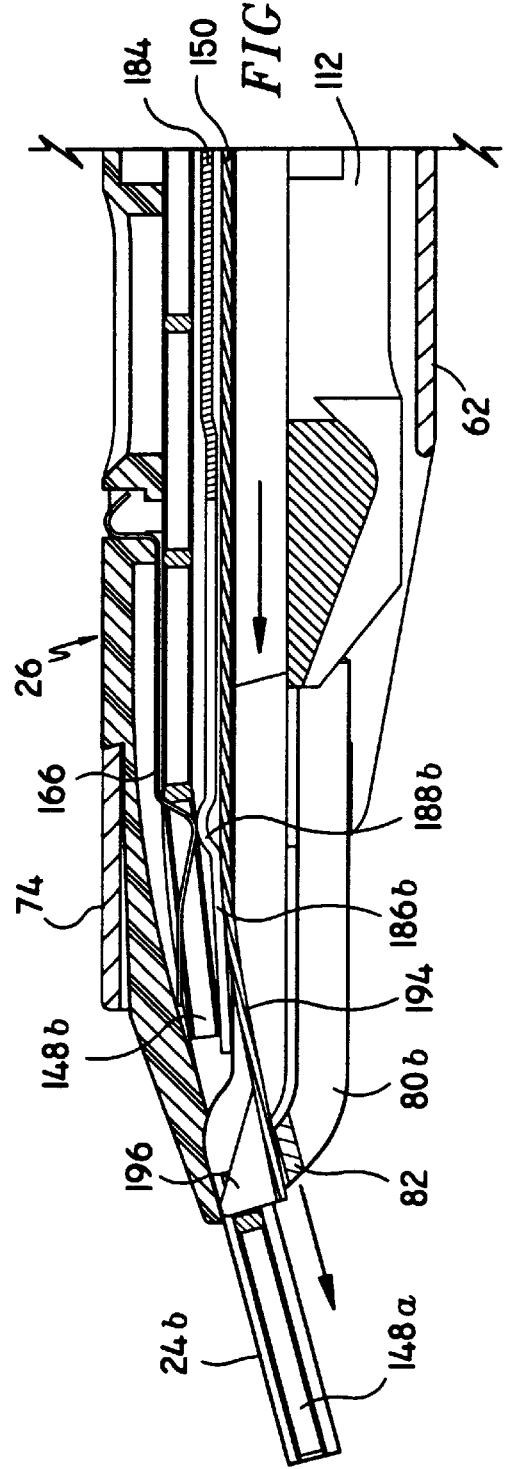

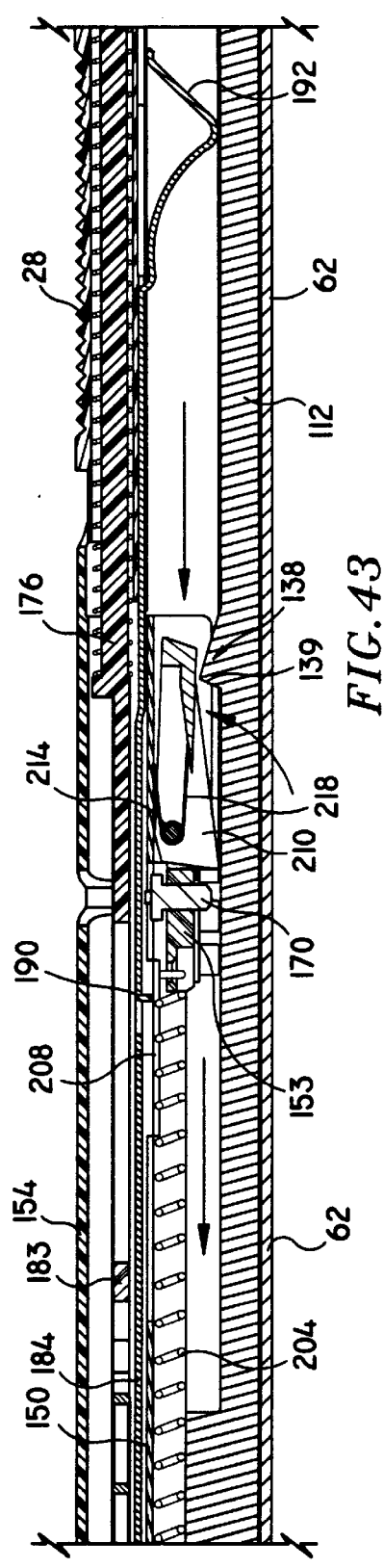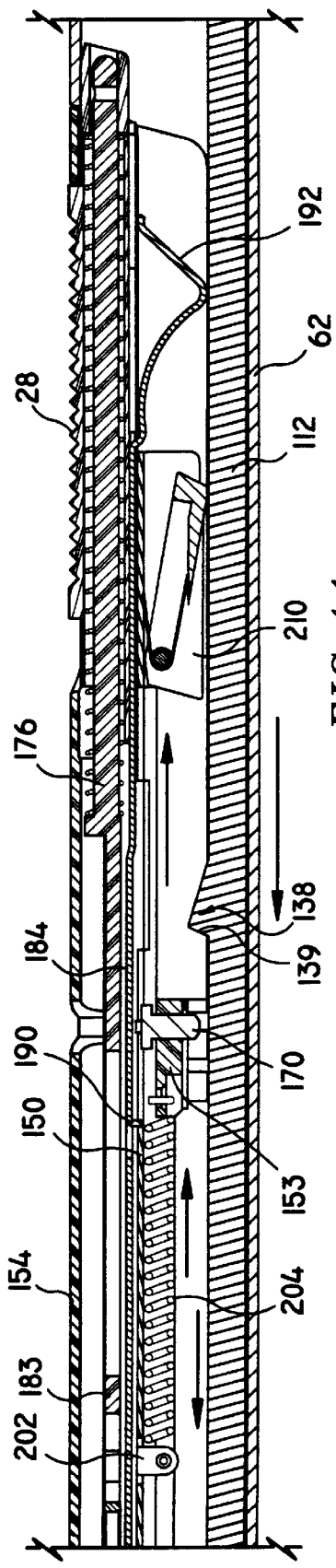

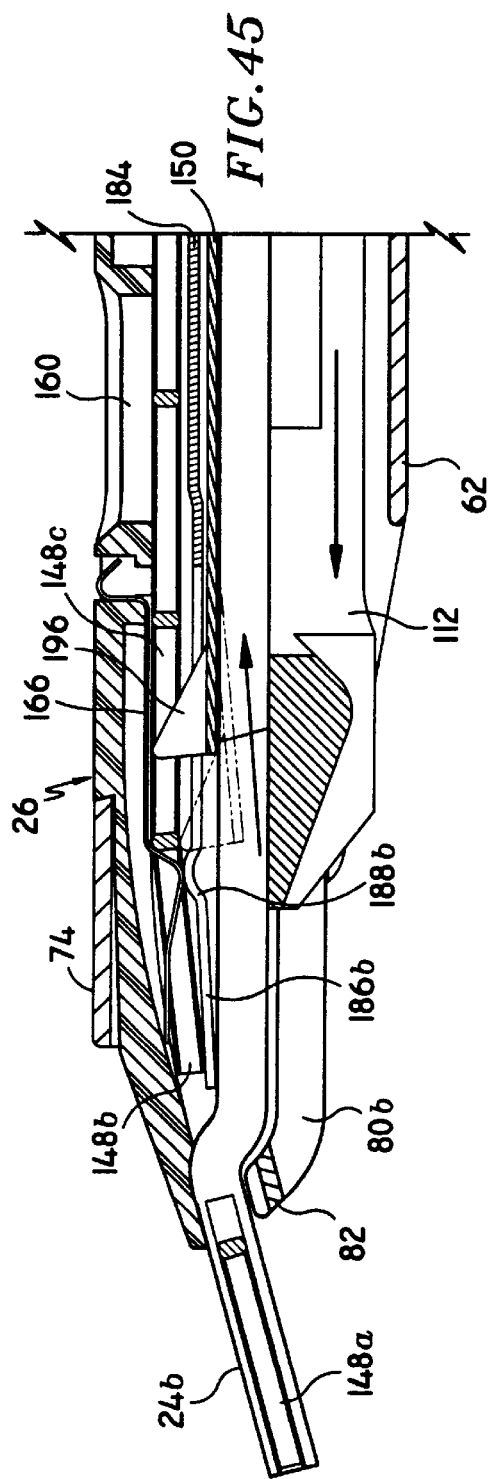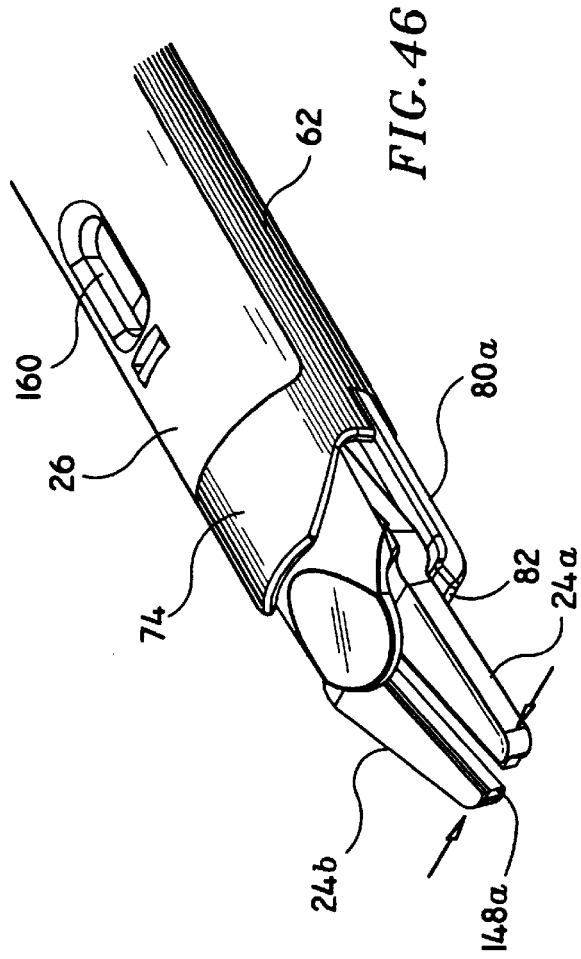

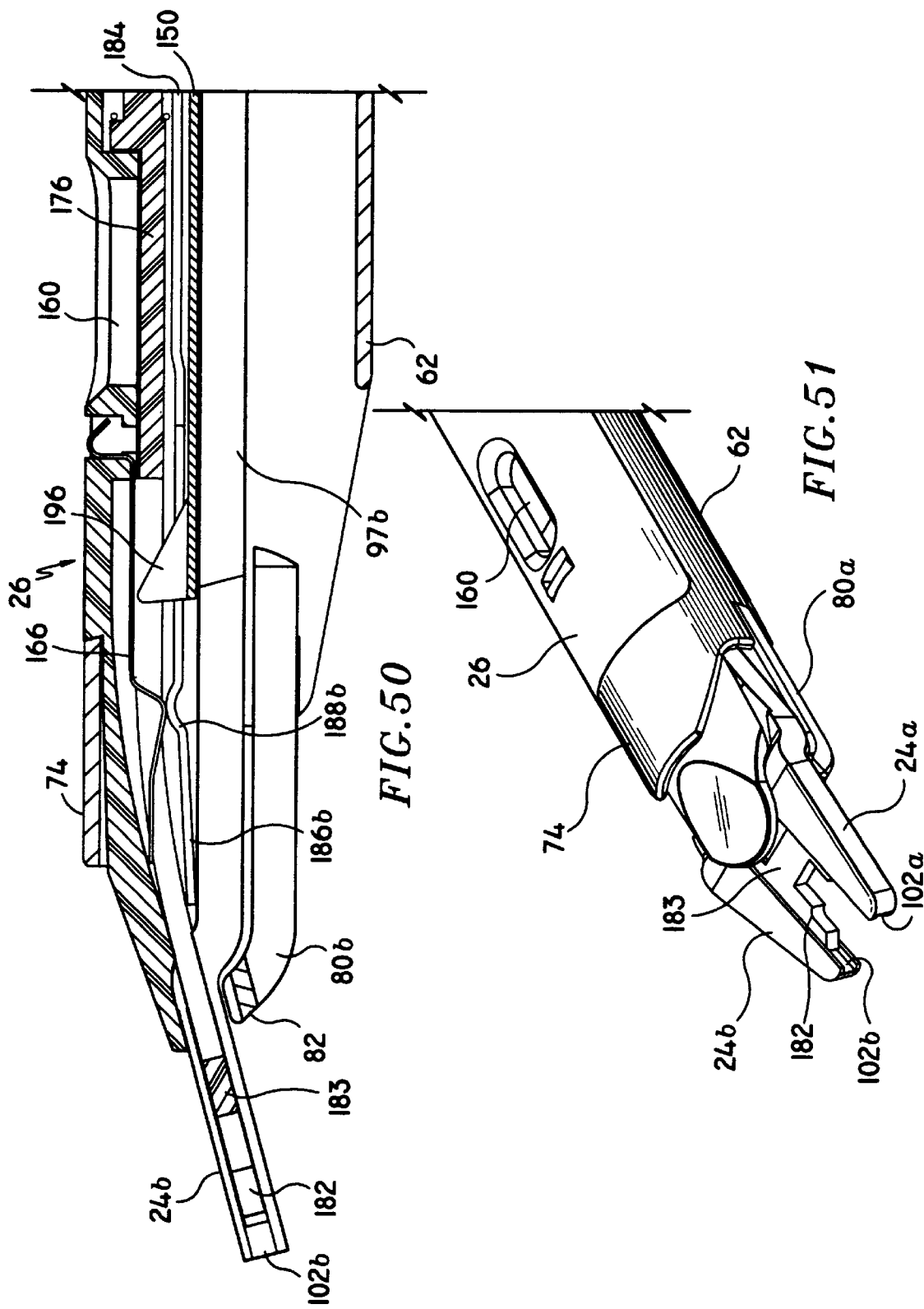

APPARATUS FOR APPLYING SURGICAL CLIPS

BACKGROUND

1. Technical Field

The present disclosure relates to apparatus for applying surgical clips to body tissue. In particular, the disclosure relates to surgical clip appliers having a replaceable unit for storing a plurality of surgical clips therein.

2. Description of Related Art

In the case of laparoscopic surgical procedures, access to the interior of the abdomen is achieved through narrow tubes or cannulas inserted through a small entrance incision in the skin. Minimally invasive procedures performed elsewhere in the body are often generally referred to as endoscopic procedures. Typically, a tube or cannula device is extended into the patient's body through the entrance incision to provide an access port which allows the insertion of various surgical instruments therethrough for performing surgical procedures far removed from the incision. During these procedures, it is often necessary to apply clips to blood vessels or various ducts to prevent the flow of body fluids therethrough during the procedure.

Endoscopic clip appliers are known in the art for applying a single clip during an entry to the body cavity. Such single clip appliers are typically fabricated from stainless steel and may be re-sterilized for use in subsequent surgical procedures.

Endoscopic clip appliers that are able to apply multiple clips in endoscopic or laparoscopic procedures during a single entry into the body cavity are described in commonly-assigned U.S. Pat. Nos. 5,084,057 and 5,100,420 to Green et al., the disclosures of which are hereby incorporated by reference herein. Another multiple endoscopic clip applier is disclosed in commonly-assigned copending U.S. patent application Ser. No. 08/134,347, filed Oct. 8, 1993 by Pratt et al., the contents of which are also hereby incorporated by reference herein. These devices are typically, though not necessarily, used during a single surgical procedure.

It is often desirable to provide a multiple endoscopic clip applier that may be reused during successive surgical procedures. In particular, the internal structure of the instrument should be configured to facilitate and simplify disassembly and resterilization.

U.S. patent application Ser. No. 08/515,341 to Pier et al., the disclosure of which is hereby incorporated by reference herein, discloses a re-sterilizable surgical clip applier which advances and forms multiple clips during a single insertion into the body cavity. This resterilizable clip applier is configured to receive and cooperate with an interchangeable clip magazine so as to advance and farm multiple clips during a single entry into a body cavity.

Endoscopic or laparoscopic procedures are-often performed remotely from the incision. Consequently, application of clips may be complicated by a reduced field of view or reduced tactile feedback for the user at the proximal end of the device. It is therefore desirable to improve the operation of the instrument by providing indication to the user of the progressive advancement of an individual clip as well as the depletion of the clip supply contained in the loading unit. It is also desirable to facilitate the complete deformation of a surgical clip prior to advancement of a second surgical clip.

SUMMARY

The subject disclosure is directed to a unique surgical clip applying instrument which includes a handle assembly and an elongated body portion extending distally from the handle assembly. A jaw assembly is mounted at a distal end portion of the elongated body portion, and includes first and second jaws movable between an open position and a closed position. The subject surgical clip applying instrument further includes an actuator which is slidable within the elongated body portion in response to actuation of the handle assembly. The actuator has camming structure at a distal portion thereof for moving the first and second jaws between the open position and the closed position.

The subject surgical clip applying instrument further includes a loading unit releasably mounted to the elongated body portion and storing a plurality of surgical clips therein. The loading unit has a clip advancer having a portion engageable with the actuator and movable therewith for advancing a distalmost surgical clip. The loading unit also has a ratchet assembly associated with the clip advancer to index progressive movement thereof.

In a preferred embodiment, the actuator further includes a protrusion configured to engage a portion of the clip advancer. The portion of the clip advancer engageable with the actuator may be a pivoting latch member disposed on the clip advancer. The ratchet assembly preferably includes a rack member disposed on the clip advancer and a pawl member disposed on the loading unit.

An additional feature of the subject surgical clip applying instrument is the provision of a novel bridge portion mounted to the distal end portion of the elongated body portion adjacent the first and second jaws. In a preferred embodiment, the bridge portion includes a transverse member in approximation with the first and second jaw portions.

In a preferred embodiment of the subject surgical clip applier, the loading unit further includes a barrier member slidable within the loading unit and advanceable into a space defined between the first and second jaws in the open position to inhibit closure thereof. The barrier member is preferably biased towards a distal end of the loading unit.

These and other features of the subject surgical apparatus will become more readily apparent to those skilled in the art from the following detailed description of the subject disclosure.

BRIEF DESCRIPTION OF THE DRAWINGS

Various embodiments of the subject surgical apparatus are described with reference to the drawings wherein:

FIG. 4 is a perspective view with parts separated of the body portion, illustrating the channel member and jaw assembly;

FIG. 5 is a perspective view with parts separated of the tube housing;

FIG. 6 is an enlarged perspective view of the driver;

FIG. 7 is an enlarged perspective view of the jaw retainer disposed on the tube housing;

FIG. 14A is an enlarged perspective view of the distal portion of the loading unit housing;

FIG. 16 is a perspective view of the cover plate;

FIG. 16A is an enlarged perspective view of the cover plate of FIG. 16;

FIG. 17 is a perspective view from above of the clip pusher assembly;

FIG. 17A is an enlarged perspective view of the clip engaging portion of the clip pusher assembly;

FIG. 20 is a perspective view from above with parts separated of the pawl and bracket;

FIG. 20A is a perspective view from below with parts separated of the pawl and bracket of FIG. 20;

FIG. 21 is a perspective view from below of the loading unit;

FIG. 21A is an enlarged perspective view of the loading unit, illustrating the ratchet assembly;

FIG. 21B is an enlarged perspective view from below of the distal end portion of the loading unit;

FIG. 21C is an enlarged perspective view from below of the proximal end portion of the loading unit;

FIG. 22 is a perspective view of the loading unit separated from the body portion;

FIG. 23 is a perspective view of the loading unit mounted on the body portion;

FIG. 24 is a perspective view of the loading unit mounting portion;

FIG. 25 is a cross-sectional view of the handle portion with the body portion removed;

FIG. 26 is a cross-sectional view of the handle portion, illustrating the pivoting handle hyperextended forward to receive the body portion;

FIG. 27 is a cross-sectional view of the handle portion of the subject surgical clip applier disposed in the neutral configuration;

FIG. 28 is an enlarged perspective view in partial cross-section, illustrating the interaction of the rotating knob with the body portion;

FIG. 29 is a perspective view of the subject surgical clip applier, illustrating the rotation of the body portion;

FIG. 30 is a plan view of the subject surgical clip applier;

FIG. 31 is a cross-sectional view of the body portion and loading unit taken along line 31—31 of FIG. 30, prior to advancement of the distalmost surgical clip;

FIG. 32A is an enlarged cross-sectional view of the distal end of the body portion and of the loading unit of FIG. 31;

FIG. 32B is an enlarged cross-sectional view of the body portion and the loading unit of FIG. 31;

FIG. 33 is a cross-sectional view taken along line 33—33 of FIG. 32B;

FIG. 34 is a cross-sectional view taken along line 34—34 of FIG. 32B;

FIG. 35 is a side view of the subject surgical clip applier, illustrating closure of the pivoting handle;

FIG. 36 is a cross-sectional view of the subject surgical clip applier, illustrating closure of the pivoting handle;

FIG. 37 is a cross-sectional view of the body portion and loading unit, illustrating the interaction of the channel member and clip pusher;

FIG. 38 is a plan view of the ratchet assembly of the loading unit;

FIG. 39 is a plan view of the ratchet assembly of FIG. 38, illustrating pivoting of the pawl member in response to translation of the clip pusher;

FIG. 40 is an enlarged cross-sectional view of the ratchet assembly of FIG. 39;

FIG. 41 is an enlarged cross-sectional view of the distal end of the body portion and loading unit, illustrating the engagement of the clip pusher and a distalmost clip;

FIG. 42 is an enlarged cross-sectional view of the distal end of the body portion and loading unit, illustrating the advancement of the distalmost clip into the jaw assembly;

FIG. 43 is an enlarged cross-sectional view of the body portion, illustrating the latch member pivoting out of engagement with the channel member;

FIG. 44 is an enlarged cross-sectional view of the body portion, illustrating the clip pusher returning proximally;

FIG. 45 is a cross-sectional view of the distal end of the clip pusher returning proximally;

FIG. 46 is an enlarged perspective view of the closure of the jaw assembly to deform a clip;

FIG. 50 is an enlarged cross-sectional view of the distal end of the body portion and the loading unit, illustrating the advancement of the clip follower into the jaw assembly; and FIG. 51 is an enlarged perspective view of the clip follower disposed in the jaw assemblies.

DETAILED DESCRIPTION OF PREFERRED EMBODIMENTS

Figure 1:
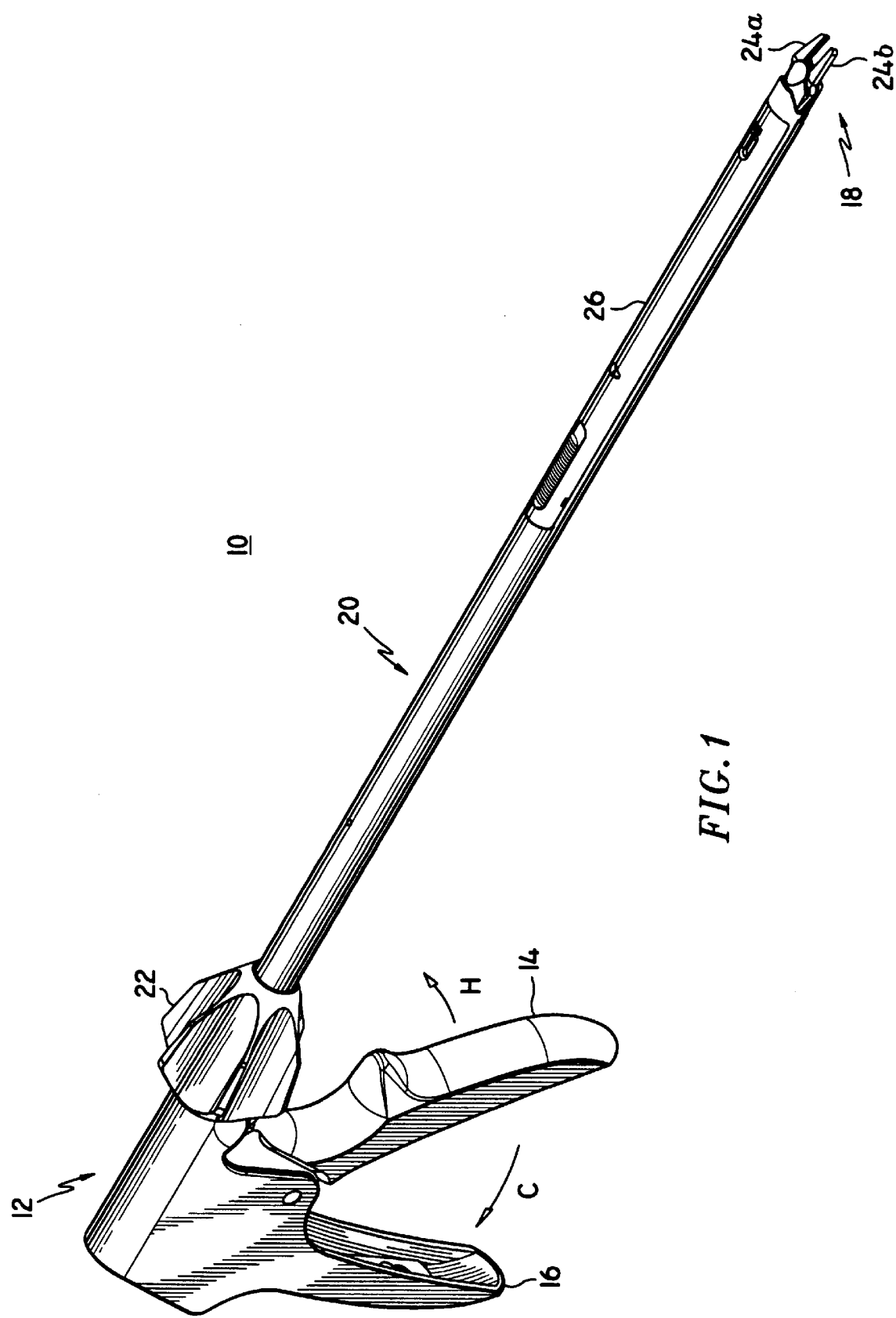
FIG. 1 is a perspective view of a surgical clip applier constructed in accordance with a preferred embodiment of the subject disclosure.

The preferred embodiments of the apparatus disclosed herein will be discussed in terms of endoscopic procedures and apparatus. However, use herein of terms such as "endoscopic" or "laparoscopic" should not be construed to limit the present application to an apparatus for use in conjunction with an endoscopic tube. In addition, it is believed that the present apparatus may find use in thoracic or arthroscopic surgery wherein access to the surgical site is achieved through a narrow cannula, or a small incision.

In the drawings and in the description which follows, the term "proximal," as is traditional, will refer to the end of the apparatus which is closest to the operator, while the term "distal" will refer to the end which is furthest from the operator.

Referring now in detail to the drawings in which like reference numerals identify similar or identical elements, a preferred embodiment of the clip applying instrument of the subject disclosure is illustrated in FIG. 1, and is designated generally by reference numeral 10. Clip applying instrument 10 includes handle portion 12 having pivoting or movable handle 14 and stationary handle 16. Manipulation of those handles 14, 16 actuates a jaw assembly 18, through elongated body portion 20. A fluted rotation collar 22 is provided adjacent handle assembly 12 for remotely varying the axial orientation of the jaw assembly 18 relative to handle assembly 12. Jaw assembly 18 includes first and second juxtaposed jaw portions 24a and 24b, which are movable between an approximated configuration in which jaw portions 24a and 24b are in relatively close relation to one another and a spaced configuration in which jaw portions 24a and 24b are separable at least a sufficient distance to receive a surgical clip therebetween.

A plurality of surgical clips is stored in loading unit 26 which is releasably mounted to elongated body portion 20. In a preferred embodiment, loading unit 26 is disposable subsequent to depletion of the supply of clips stored therein. The remainder of instrument 10, namely handle portion 12 and body portion 20 may be disassembled, resterilized and reused in combination with another loading unit containing a supply of clips.

Movable handle 14 is shown in a neutral or "at rest" position with respect to stationary handle 16. Pivoting movement of movable handle 14 in the direction of arrow "C" towards stationary handle 16 from the neutral position defines a closing stroke. During this closing stroke, a distalmost surgical clip is advanced between the spaced apart jaw portions 24a and 24b. Further closure of movable handle 14 approximates jaw portions 24a and 24b to deform the clip. Pivoting movement of movable handle 14 from the neutral position away from the stationary handle in the direction of arrow "H" to a hyperextended position releases body portion 20 from handle portion 12 for separation and sterilization, as will be described below.

Figure 2:
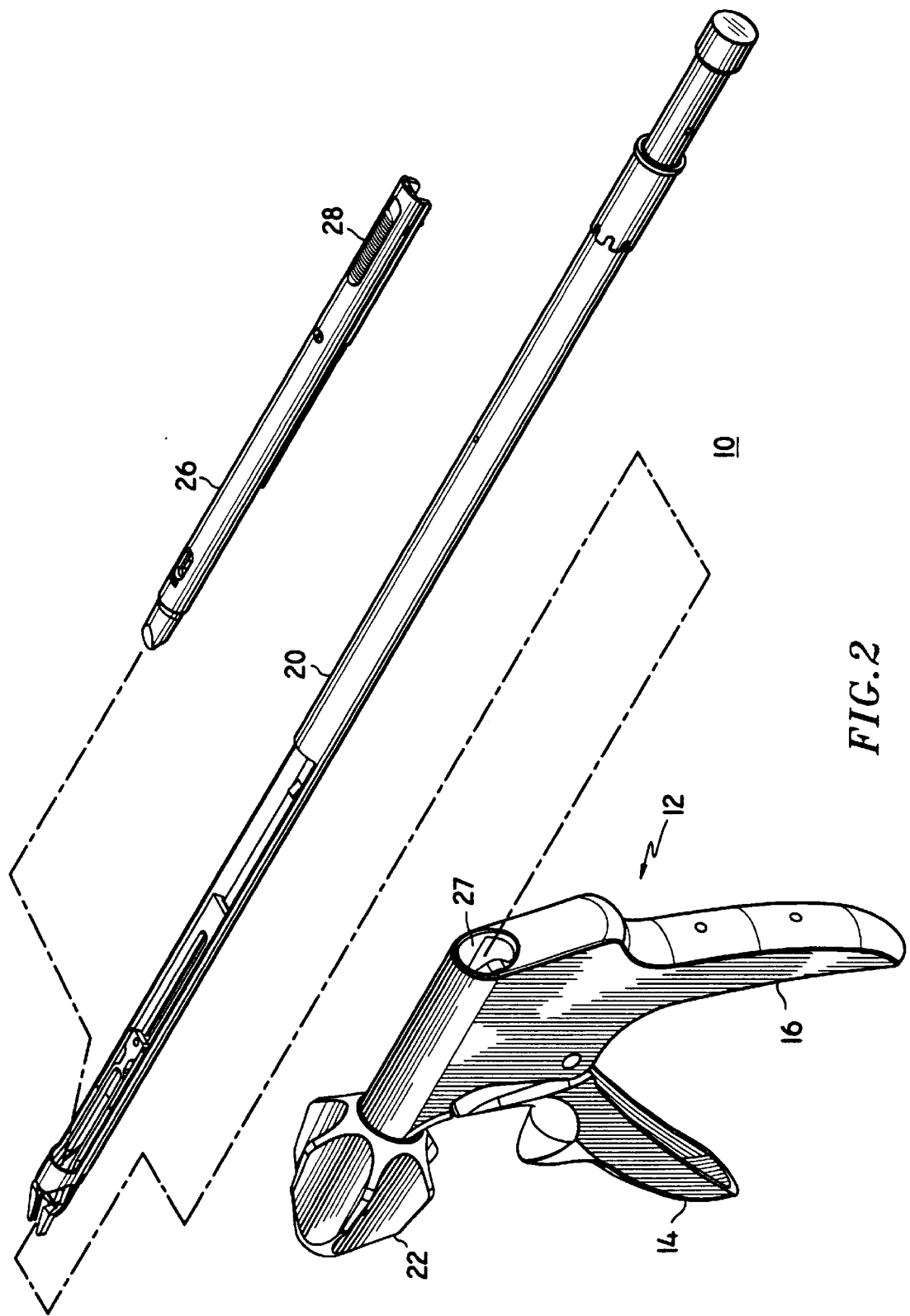
FIG. 2 is a perspective view of the surgical clip applier of FIG. 1, illustrating the loading unit and the body portion separated from the handle portion.

With reference to FIG. 2, surgical clip applying instrument 10 is shown separated into component subassemblies, i.e. handle portion 12, body portion 20, and loading unit 26. As described above, hyperextension of pivoting handle 14 permits body portion 20 to be slidably removed from proximal end of bore 27 of handle portion 12. Loading unit 26 is removed from body portion 20 by actuation of release lever 28, as will be described in detail below.

The Handle Portion

Figure 3:
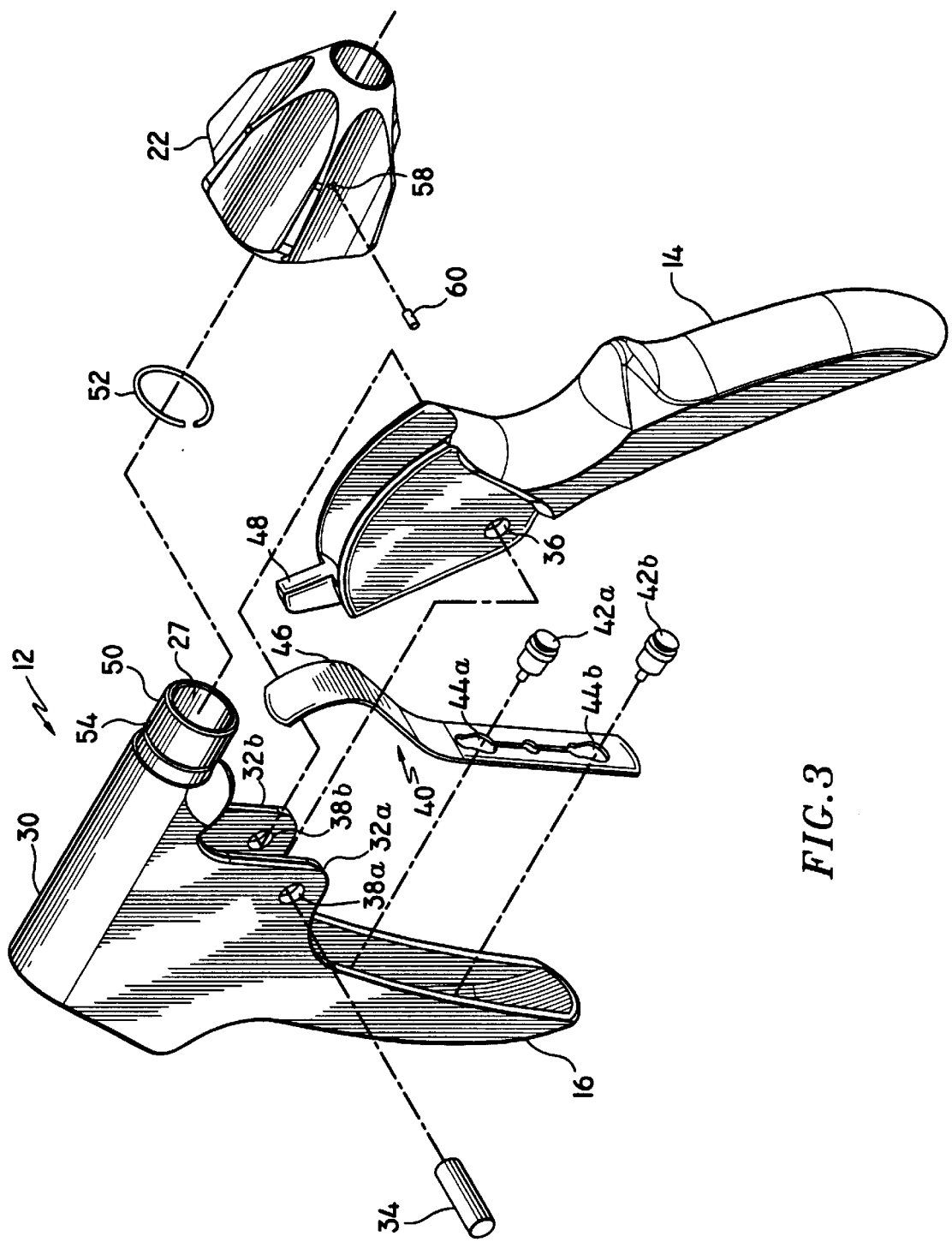
FIG. 3 is a perspective view with parts separated of the handle portion.

Turning now to FIG. 3, the components of handle portion 12 are illustrated. Handle portion 12 is designed to facilitate ease of disassembly and thorough resterilization prior to re-use. Handle portion 12 includes housing 30, having bore 27 extending therethrough. Stationary handle 16 depends from housing 30. Pivoting handle 14 is mounted to shackles 32a and 32b of housing 30 by pivot pin 34, which passes through aperture 36 in pivoting handle 14 and apertures 38a and 38b in shackles 32a and 32b, respectively. Housing 30 and pivoting handle 14 are preferably formed from a biocompatible metallic alloy which is capable of withstanding repeated resterilization procedures.

Leaf spring 40 is mounted adjacent stationary handle 16 by a pair of retainer pins 42a and 42b. Leaf spring 40 preferably includes a pair of keyhole-shaped apertures 44a and 44b which facilitate locking engagement of spring 40 with retainer pins 42a, 42b and removal therefrom for resterilization. A curved portion 46 of leaf spring 40 contacts tab 48 to normally bias pivoting handle 14 in the neutral position. Tab 48 extends at least partially into bore 27 to maintain body portion 20 therein. When pivoting handle is hyperextended, i.e. pivoted away from stationary handle 16 such that tab 48 acts against the bias of leaf spring 40, tab 48 is directed out of bore 27 to permit removal of body portion 20 from housing 30.

Rotation knob 22 is rotatably mounted to housing 30 at mounting sleeve 50, which is formed surrounding the distal portion of bore 27 and dimensioned to receive rotation knob 22. Clip 52 is dimensioned to fit over annular notch 54 in mounting sleeve 50. Rotation knob 22 also includes an annular notch (not shown), which permits rotation knob 22 to be rotatably mounted to sleeve 50 in a snap-fitting arrangement. Rotation knob 22 further includes transverse bore 58 for the reception of pin 60, which interlocks with body portion 20 to effect rotational motion, as will be described in greater detail below.

The Body Portion

With reference to FIG. 4, the elongated body portion 20 is configured to be releasably mounted within handle portion 12 and to be disassembled to facilitate resterilization. Body portion 20 includes outer sleeve 62 defining a distal cutaway portion 64 for reception of loading unit 26. (See, FIG. 2) Outer sleeve 62 encloses channel member subassembly 66, which is configured to advance surgical clips from loading unit 26 and to actuate jaw assembly 18 to receive and deform the surgical clips. The terms "top" or "upper" shall describe that portion of body portion 20 in proximity with loading unit 26, whereas the terms "bottom" and "lower" shall refer to the opposed portion of body portion 20.

Turning now to FIG. 5, a proximal end portion of elongated outer sleeve 62 receives driver 67, which is substantially cylindrical. As illustrated in FIG. 6, the distal portion of driver 67 includes a plurality of crenelations 68 to engage with pin 60 of rotation knob 22 as will be described below. The proximal portion of driver 67 includes annular flange 70 to engage with a shoulder portion of bore 27 of handle portion 12. Driver 67 is dimensioned to provide a tight frictional fit surrounding the proximal end portion of outer sleeve 62. Alternatively, it is contemplated that driver 67 may be welded or otherwise secured to sleeve 62.

Distal nose portion 72 of outer sleeve 62 is configured to support loading unit 26 and jaw assembly 18. In particular, distal nose portion 72 includes retainer band 74 for securing the distal end of loading unit 26 in proper position. In addition, distal nose portion 72 includes notches 76a and 76b for reception of bridge member 78. Bridge member includes a pair of proximally extending arms 80a and 80b configured to fit within notches 76a and 76b, respectively, and transversely extending support bar 82, which is in approximation with jaw assembly 18, as will be described in greater detail below.

With continued reference to FIG. 5 in conjunction with FIG. 7, the bottom surface of outer sleeve 62 includes aperture 84 for reception of jaw retainer 86, having channel 88 for releasably mounting of jaw assembly 18 to outer sleeve 62. Outer sleeve 62 further includes aperture 90 on an upper surface thereof for reception of retaining pin 92, which engages a portion of channel member subassembly 66 as will be described below.

Figure 8:
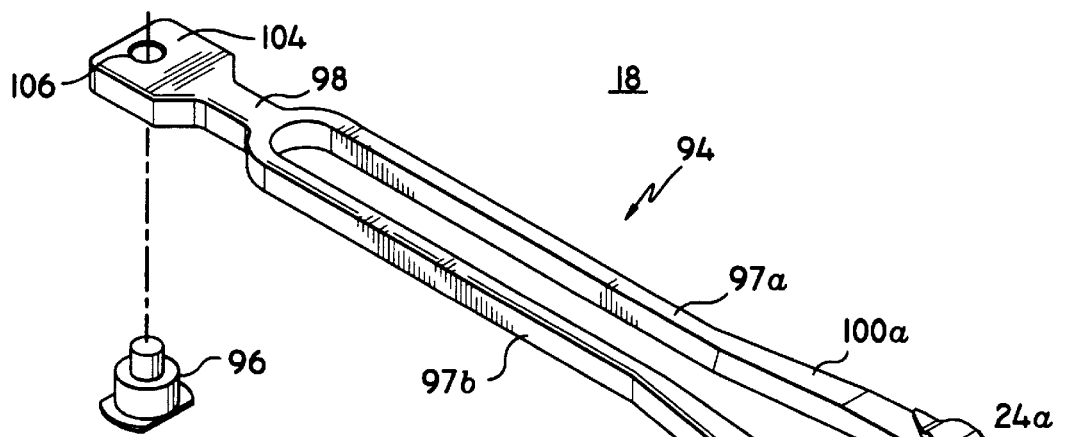
FIG. 8 is a perspective view from above with parts separated of the jaw assembly.
Figure 9:
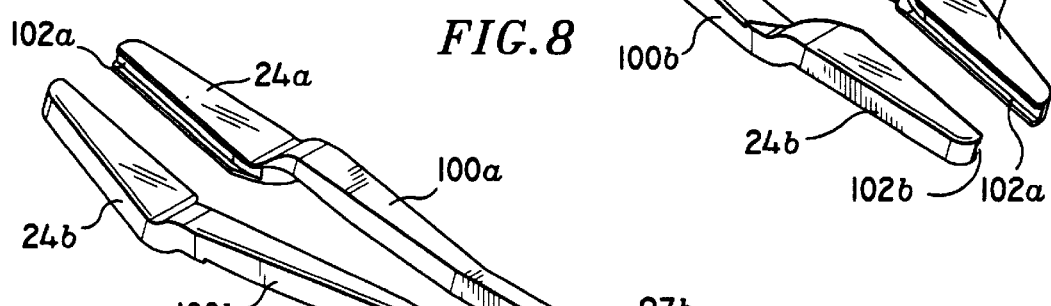
FIG. 9 is a perspective view from below of the assembled jaw assembly.

With reference to FIGS. 8 and 9, jaw assembly 18 is illustrated with constituent parts, i.e. jaw member 94 and key 96. Jaw member 94 includes first and second shank portions 97a and 97b joined at crown portion 98. Juxtaposed jaw portions 24a and 24b are disposed at the distal end portions of shank portions 97a and 97b. Resilience in the material, e.g. stainless steel, used to construct shank portions 97a and 97b permits relative approximation and spacing of jaw portions 24a and 24b. Preferably, shank portions 97a and 97b are normally biased in a spaced apart configuration. First and second shank portions 97a and 97b each include a longitudinally tapering camming surface 100a and 100b for control of relative approximation of jaw portions 24a and 24b in conjunction with channel member subassembly 66.

Jaw portions 24a and 24b each define an elongated channel 102a and 102b on the inner surfaces thereof for reception of a surgical clip. Crown portion 98 includes a proximally extending mounting tab 104 having transverse aperture 106 for the reception of key 96. As illustrated in FIG. 9, key 96 includes a cylindrical portion 108 adjacent mounting tab 104 to cooperate with channel member subassembly 66, and mounting flange 110 for mounting in channel 88 of jaw retainer 86.

Figure 10:
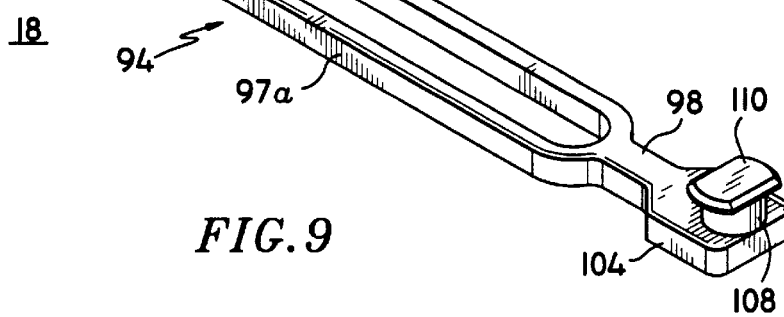
FIG. 10 is an enlarged perspective view of the distal end of the tube housing and bridge portion.
Figure 11:
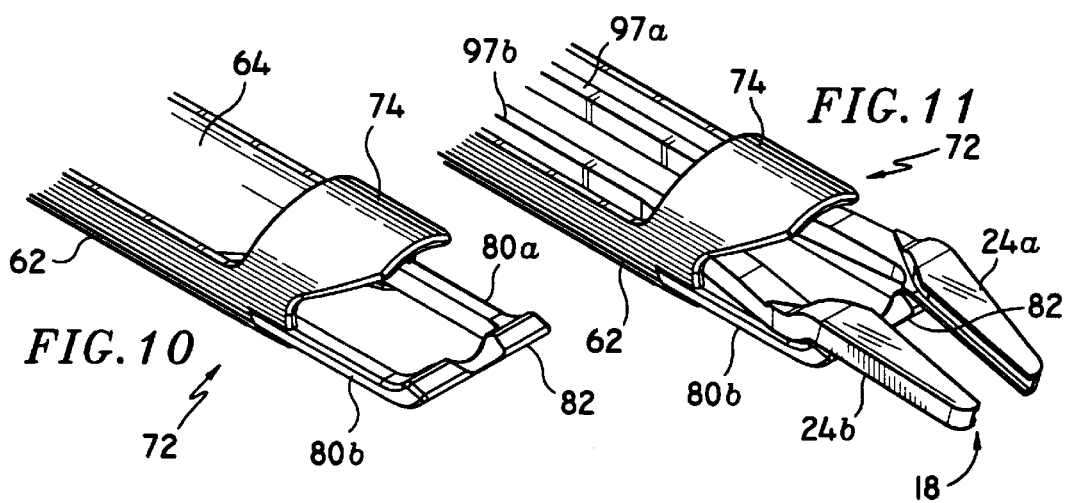
FIG. 11 is an enlarged perspective view of the tube housing and bridge portion of FIG. 10, illustrating the jaw assembly in position.

Turning now to FIGS. 10 and 11, jaw assembly 18, as mounted in jaw retainer 86 (FIG. 5), extends distally beyond nose portion 72 of outer sleeve 62. Jaw portions 24a and 24b are positioned adjacent transverse support member 82 of bridge member 78. Juxtaposition of jaw portions 24a and 24b with transverse support member 82 inhibits undesirable twisting of jaw portions 24a and 24b during surgical clip application or during contact with resistant tissue.

Figures 12, 13:
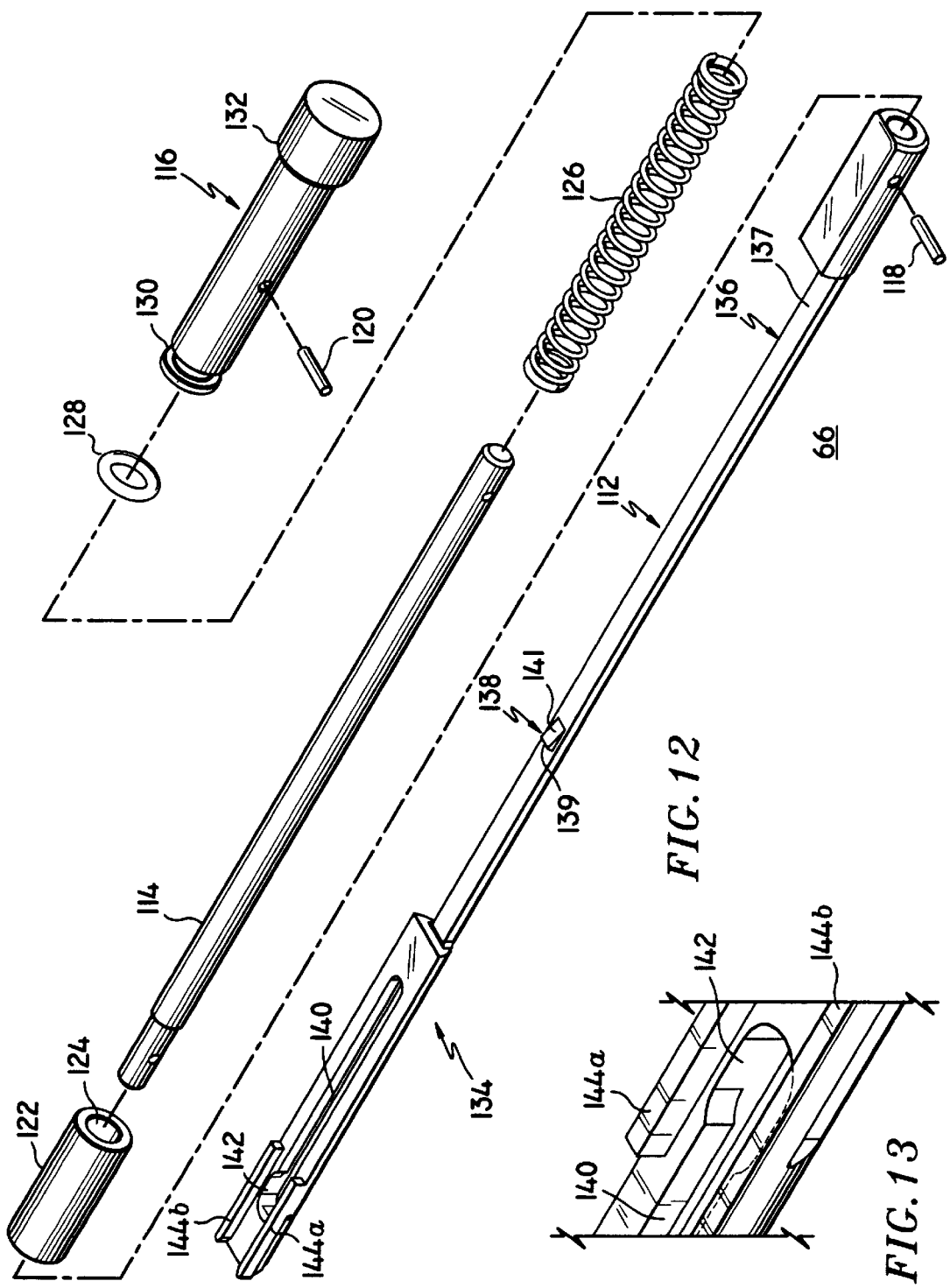
FIG. 12 is a perspective view with parts separated of the channel member assembly.
FIG. 13 is an enlarged perspective view of a distal portion of the channel member illustrating a slot for cooperating with the jaw assembly.

As illustrated in FIG. 12, channel member subassembly 66 includes channel member 112, rod 114 and activating pin 116. Distal end of rod 114 is secured to channel member 112 by securement pin 118, and proximal end of rod 114 is secured to activating pin 116 by securement pin 120. Collar 122 is constructed with center bore 124 to be longitudinally slidable over rod 114. Collar 122 is limited in its distal travel by channel member 112 and in its proximal travel by activating pin 116. Return spring 126 is slidable over rod 114 and is configured to normally bias collar 122 distally. Collar 122 is configured to engage retaining pin 92 in outer sleeve 62 to normally bias channel member subassembly 66 proximally, as will be described below. A seal is provided to prohibit the escape of gases and fluids from the operative site. Preferably, o-ring 128 is provided to fit over annular notch 130 in activating pin 116 to provide the required seal. Annular shoulder portion 132 is formed at a proximal portion of activating pin to limit the distal travel of channel member subassembly 66 within outer tube 62.

Channel member 112 is configured to advance surgical clips from loading unit 26 (FIG. 2) and to control the relative movement of jaw portions 24a and 24b. Channel member 112 further includes distal portion 134 and intermediate portion 136. Intermediate portion 136 has a substantially flattened upper surface 137 and a reduced cross-section to accommodate the components of loading unit 26 within the circumference of outer tube 62. Protrusion 138 is formed on the upper surface 137 of intermediate portion 136 to transfer longitudinal displacement to the loading unit 26. Preferably, protrusion 138 includes a substantially vertical distal face 139 and a substantially more shallow sloping proximal face 141.

With continued reference to FIG. 12 in conjunction with FIG. 13, distal portion 134 of channel member 112 is configured to accommodate and control jaw assembly 18 (FIG. 1). Distal portion 134 includes longitudinally elongated keyhole slot 140 terminating at its distal end in an enlarged oval shaped aperture 142. When channel member 112 is at a proximal location, aperture 142 is positioned adjacent aperture 84 in outer tube 62 (FIG. 5). Aperture 142 is sized to permit jaw retainer 86 to pass therethrough for mounting to tube 62 at aperture 84 in conjunction with jaw assembly 18. Slot 140 is sized to prevent jaw retainer 88 from displacing itself upward from aperture 84, but is dimensioned to permit channel member 112 to slide relative to cylindrical portion 108 of key 96. Distal portion 134 further includes a pair of upright camming flanges 144a and 144b which cooperate with camming surfaces 100a and 100b of a jaw member 94 to move jaw portions 24a and 24b into approximation upon longitudinal displacement of channel member 112, as will be described below.

The Loading unit subassembly

Figure 14:
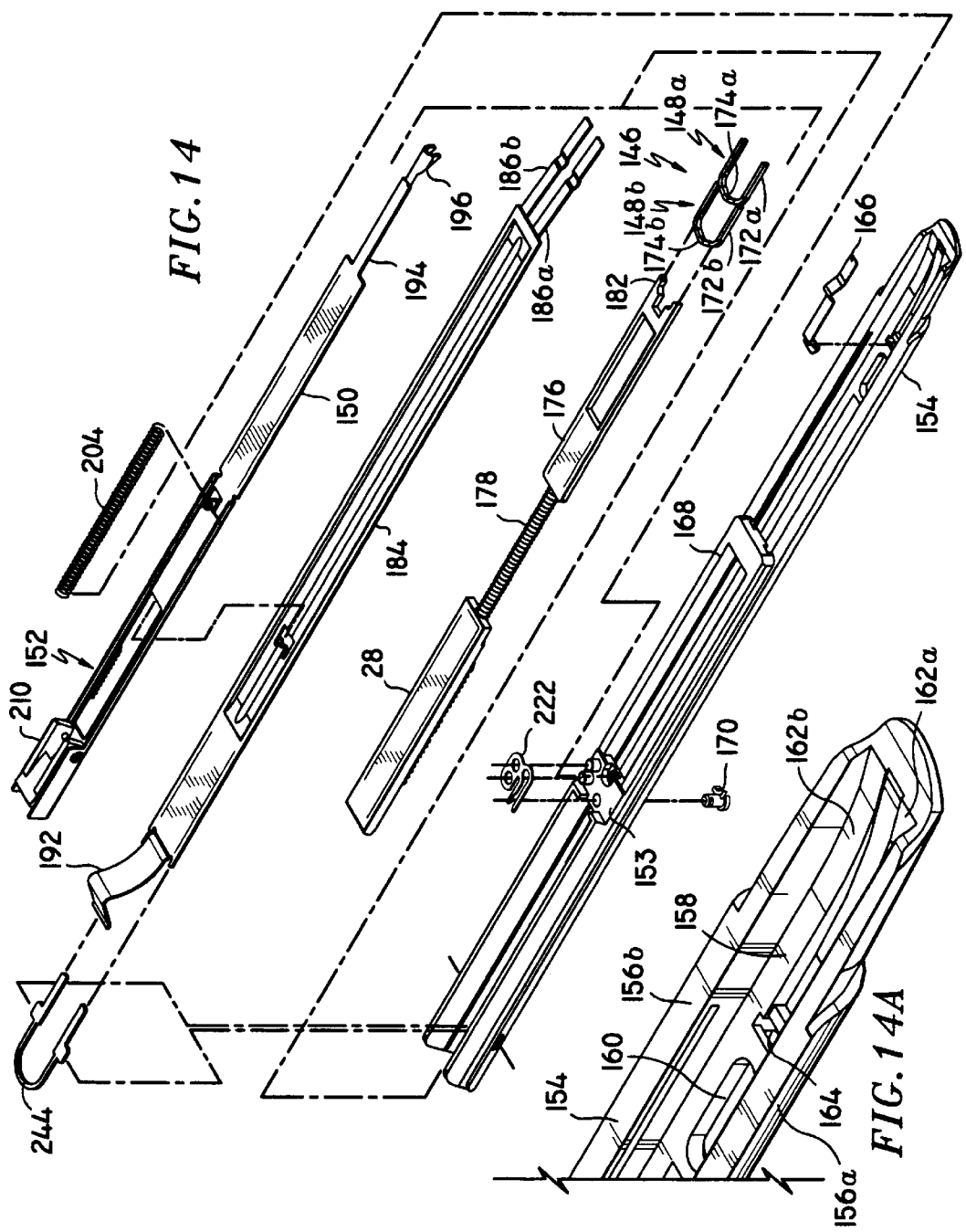
FIG. 14 is a perspective view with parts separated of the loading unit of the subject clip applier.

Turning now to FIG. 14, a preferred embodiment of loading unit 26 is illustrated. As described above, handle portion 12 and endoscopic body portion 20 are constructed to simplify disassembly and resterilization. Loading unit 26, however, is preferably constructed as a replaceable element which is disposed of after use. The functions of storing stack 146 of surgical clips 148a and 148b, of housing the clip pusher or clip advancer 150, and of supporting a ratchet mechanism 152 to index progressive deployment of distalmost surgical clip 148a are performed by loading unit 26.

The internal components of loading unit 26 are supported within cartridge housing 154 which is preferably molded or machined from an engineering plastic. As illustrated in FIG. 14A, cartridge housing 154 includes a pair of side walls 156a and 156b and a top surface 158. Top surface 158 includes aperture 160 for viewing the progression of surgical clips. The distal portion of top surface 158 includes a pair of sloping guide surfaces 162a and 162b for directing surgical clip 148a. Mounting slot 164 is provided for receiving a proximal end of clip guide 166. Bottom plate 168 supports pawl member 170, as will be described below.

Figure 15:
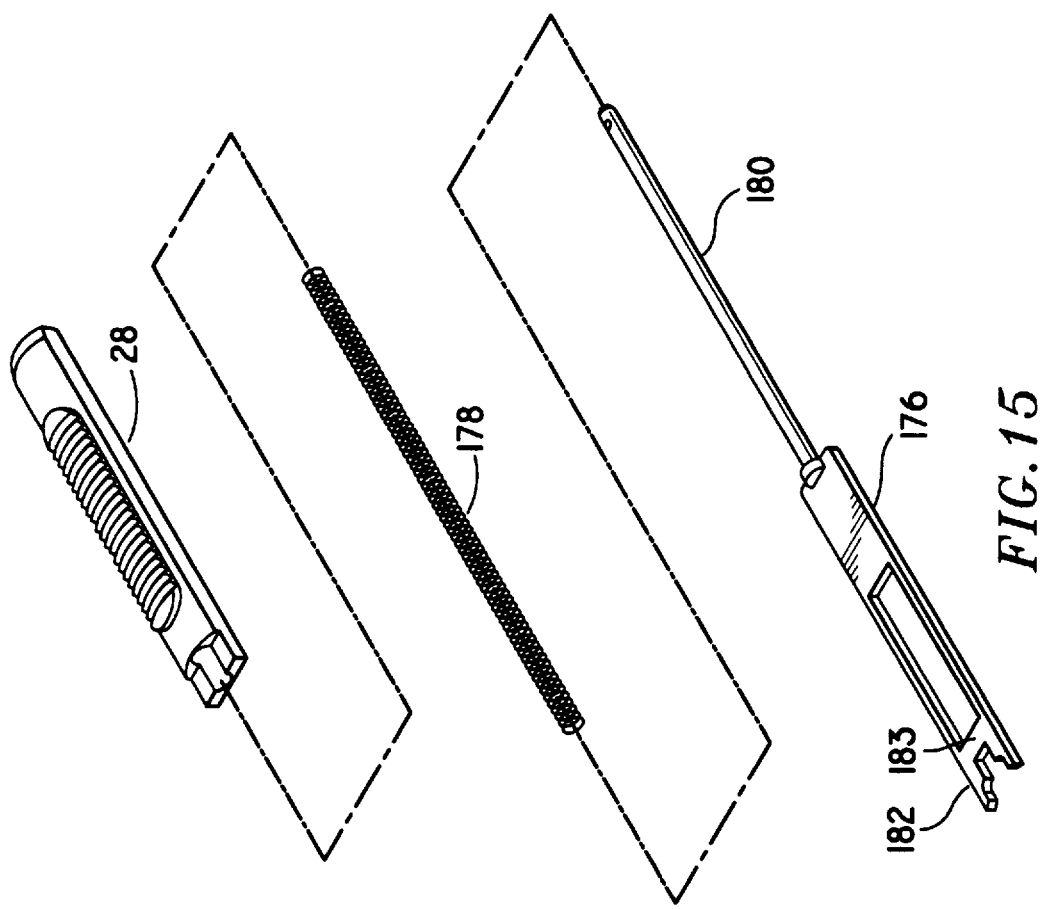
FIG. 15 is a perspective view with parts separated of the clip follower and release member.

Referring now to FIG. 14 in conjunction with FIG. 15, stack 146 of surgical clips 148a and 148b is arranged such that legs 172b of surgical clip 148b contact crown 174a of surgical clip 148a. Surgical clip stack 146 is normally biased towards the distal end of loading unit 26 by clip follower 176 and compression spring 178 which surrounds proximal supporting pin 180. Clip contacting portion 182 of clip follower 176 is bifurcated and configured to contact crown portion 174b of proximalmost surgical clip 148b. Transverse bar 183 is disposed proximal to clip contacting portion 182.

The proximal end of compression spring 178 abuts release lever 28, which is slidable within an aperture in housing 154. Sliding of release lever 28 against the bias of compression spring 178 permits the removal and mounting of loading unit 26, as will be described below.

Referring now to FIG. 16 in conjunction with FIG. 14, cover plate 184 is disposed adjacent surgical clip stack 146 and clip follower 176, and maintains surgical clip stack in alignment. The distal end portion of cover plate 184 includes a pair of guide flanges 186a and 186b to direct surgical clip 148a into the jaw portions. Transverse protrusions 188a and 188b in guide flanges 186a and 186b cooperate with clip guide 166 to act as a stop for retaining surgical clip 148a in position prior to advancement thereof by clip pusher 150.

As illustrated in FIGS. 16 and 16A, cover plate 184 includes flange 190 to limit the proximal longitudinal travel of the clip pusher. The proximal end portion of cover plate 184 includes downwardly extending leaf spring 192, which facilitates separation and removal of the loading unit from the body portion.

Figures 18, 19:
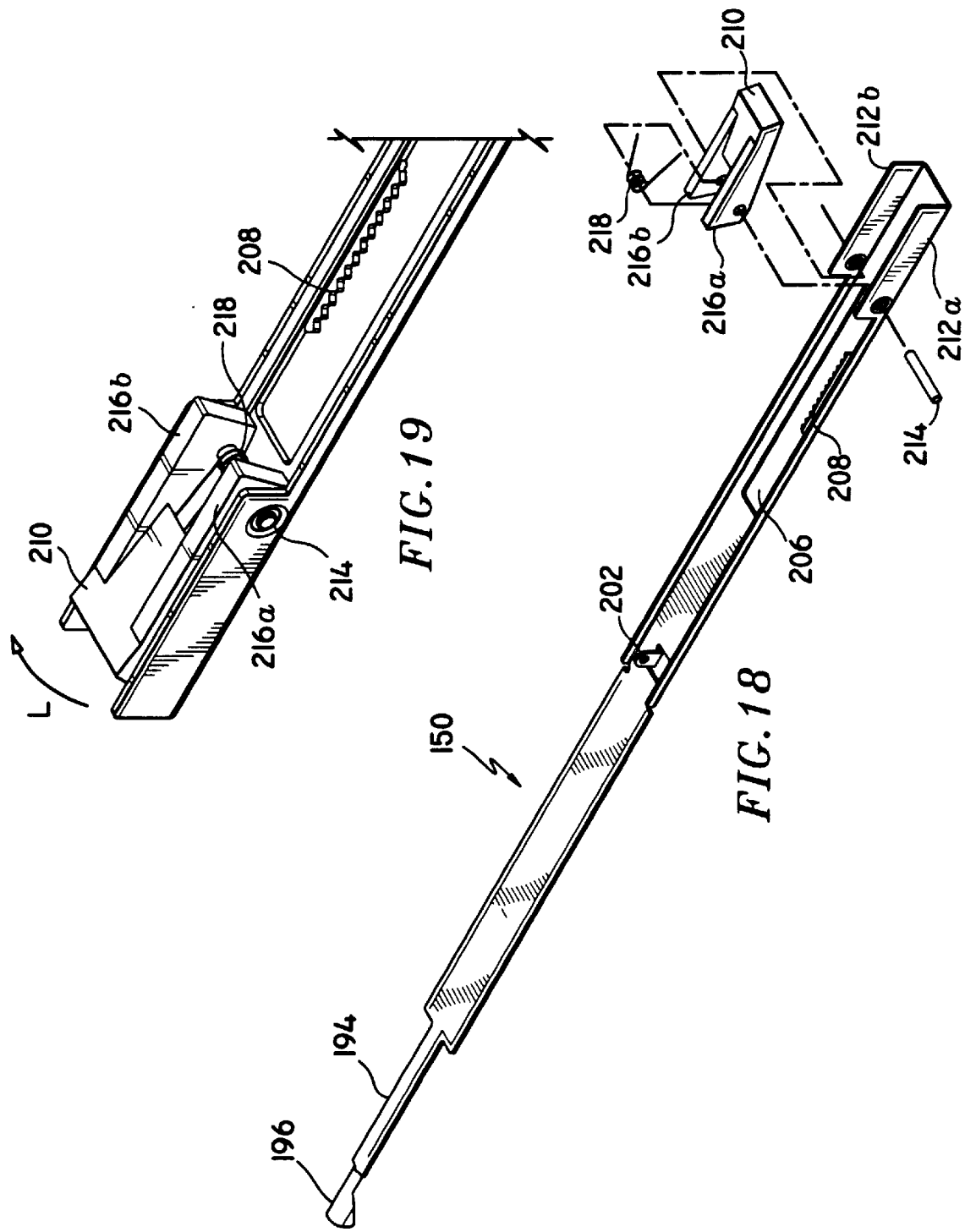
FIG. 18 is a perspective view from below with parts separated of the clip pusher assembly.
FIG. 19 is an enlarged perspective view of the clip pusher and latch member.

Referring to FIGS. 17–19, clip pusher 150 is configured to advance a surgical clip into the jaw portions. As illustrated in FIG. 17, the distal portion of clip pusher 150 includes a clip advancing arm 194 formed of a resilient material. Clip advancing arm 194 advances surgical clips through a non-linear path adjacent guide surfaces 162a and 162b of cartridge housing 154 (FIG. 14A) and into elongated channels 102a and 102b of jaw portions 24a and 24b (FIG. 8). As best seen in FIG. 17A, clip advancing arm 194 terminates in a clip engaging portion 196 having a pair of sloping trailing edges 198a and 198b and a pair of substantially vertical leading edges 200a and 200b. Clip engaging portion 196 is configured such that leading edges 200a and 200b contact crown portion 174a of surgical clip 148a.

Turning now to FIG. 18, clip pusher 150 includes a spring mounting flange 202, at which return spring 204 (not shown) is connected to normally bias clip pusher 150 proximally, as will be described below. Guide channel 206 is defined in clip pusher 150 and cooperates with flange 190 in cover plate 184 to limit the proximal range of movement of clip pusher 150. A series of ratchet teeth 208 are defined adjacent to channel 206 to increment advancement of clip pusher 150, as will be described below.

Latch member 210 is pivotably mounted at the proximal portion of clip pusher 150 by means of a pair of shackles 212a and 212b in clip pusher 150 and pivot pin 214 passing therethrough and through shackles 216a and 216b in latch member 210. Torsion spring 218 normally biases latch member 210 in a downward direction as indicated by arrow "L" in FIG. 19. Latch member 210 is configured to be contacted by protrusion 138 of channel member 112 to advance surgical clips as will be described below.

With reference to FIGS. 20–20A in conjunction with FIG. 21, ratchet assembly 152 includes pawl 170, which is mounted to bottom plate 168 at pawl mount 153 by pawl mounting bracket 222. Pawl 170 includes a substantially cylindrical portion 224 having notch 226 extending partially therethrough, and a flange portion 228 having tooth 230 for engaging rack 208 of clip pusher 150. Pawl mounting bracket 222 has a substantially "U"-shaped configuration, including a pair of arms 232a and 232b joined at crown portion 234. Arm 232a defines a pair of apertures 236a and 236b for mounting on nodes 238a and 238b of bottom plate 168. Arm 232b defines an elongated slot 240 including arcuate notch 242 for mounting pawl 170 thereto adjacent notch 226.

In the assembled configuration of loading unit 26 as illustrated in FIGS. 21 and 21A, pawl 170 extends into position adjacent rack 208 of clip pusher 150. Return spring 204 is mounted to bottom plate 168 to normally bias clip pusher 150 proximally.

With reference to FIG. 21 in conjunction with FIG. 21B, guide flanges 186a and 186b cooperate with clip guide 166 to act as a stop for retaining surgical clip 148a in position prior to advancement by clip pusher 150. Clip engaging portion 196 passes between guide flanges 186a and 186b to advance surgical clip 148a at crown 172a beyond clip guide 166 to jaw portions 24a and 24b (not shown).

With reference to FIG. 21 in conjunction with FIG. 21C, leaf spring 192 extends downwardly to provide or facilitate separation and removal of loading unit 26 from body portion 20 by providing a force against channel member 112.

Turning now to FIG. 22, loading unit 26 is mounted to body portion 20 by inserting the distal portion of cartridge housing 154 beneath retainer band 74. Release member 28 is advanced distally as indicated by arrow "M". As illustrated in FIGS. 23 and 24, release member 28 is permitted to move to its normally biased position in the direction of arrow "R" to secure loading unit 26 to body portion 20.
Operation of the Instrument FIG. 25 illustrates pivoting handle 14 in the neutral position. Tab 48 partially extends into bore 27 prior to insertion of body portion 20. As depicted in FIG. 26, hyperextension of pivoting handle 14 in the direction of arrow "H" against the bias of leaf spring 40 moves tab 48 out of the plane of bore 27. Body portion 20 is inserted into bore 27 from the proximal end of housing 30 in a distal direction as indicated by arrow "D". FIG. 27 illustrates that the distal end of activating pin 116 has been advanced distal to tab 48 until flange 70 of driver 67 contacts shoulder portion 220 of bore 27. Pivoting handle 14 is thereupon released and curved portion 46 of leaf spring 40 resumes its unbiased shape and returns pivoting handle 14 to the neutral position. Tab 48 is thereby positioned proximal to activating pin 116.

The rotation control feature of instrument 10 is illustrated in FIGS. 28–29. As depicted in FIG. 28, body portion 20 is inserted into bore 27 such that pin 60 of rotation knob 22 contacts one crenelation 68 of driver 67. The interlocking of crenelation 68 with pin 60 permits remote axial rotation of the tool assembly, as shown in FIG. 29.

FIGS. 30–34 depict the body portion 20 and loading unit 26 of instrument 10 prior to advancement of a surgical clip. FIG. 31 illustrates stack 146 of surgical clips 148a, 148b stored in loading unit 26. Channel member 112 is disposed in a proximal position. Referring to FIG. 32A, the distal portion of loading unit 26 is shown in position adjacent body portion 20. Distalmost surgical clip 148a is biased distally by compression spring 178 and held in position at crown portion 174a thereof by clip guide 166 and transverse ridges 188a (not shown) and 188b of cover plate 184. Clip engaging portion 196 of clip pusher 150 is disposed in an initial position spaced from crown portion 174a.

As illustrated in FIG. 32B, latch member 210 is biased downward into contact with channel member 112. Channel member 112 is initially disposed in a proximal position such that protrusion 138 is spaced from latch member 210. With reference to FIG. 32B in conjunction with FIG. 33, cover plate 184 maintains surgical clips 148b in proper alignment for advancement into jaw portions 24a and 24b (not shown). As illustrated in FIG. 32B in conjunction with FIG. 34, cover plate retainer clip 244 is substantially U-shaped having a pair of arms 246a and 246b including flanges 248a and 248b disposed in notches 250a and 250b in cartridge housing 154. Retainer clip 244 maintains a distal portion of cover plate 184 in position.

Turning to FIGS. 35 and 36, closure of pivoting handle 14 in the direction of arrow "C" actuates the tool assembly. As illustrated in FIG. 36, closure of pivoting handle 14 advances tab 48 in an arcuate path in a generally distal direction as indicated by arrow "D". Tab 48 contacts activating pin 116, thereby advancing activating pin 116, rod 114, and channel member 112 distally against the bias of return spring 126.

With reference to FIG. 37, channel member 112 is advanced distally as described above. Upon advancing a predetermined distance, distal surface 139 of protrusion 138 engages downwardly biased latch member 210. At that point, clip pusher 150 is conveyed distally by channel member 112 against the bias of return spring 204.

Turning now to FIGS. 38–40, operation of ratchet mechanism 152 will now be described with respect to the advancement of clip pusher 150. With reference to FIG. 38, engaging tooth 230 of pawl member 170 is normally biased by support arm 232b into engagement with rack 208 of clip pusher 150. Consequently, the position of clip pusher 150 to bottom plate 168 is maintained. As a result, if pivoting handle 14 is released, return spring 126 will return channel member 112 proximally, but clip pusher 150 and distalmost surgical clip 148a are maintained in position. Subsequent closure of handle 14 will advance channel member 112 distally and thereby reengage protrusion 138 with latch member 210. In this way, surgical clip 148a is advanced into jaw portions 24a and 24b before subsequent surgical clip 148b is advanced, thereby preventing jamming of instrument 10. As illustrated in FIGS. 39–40, advancement of clip pusher 150 pivots pawl member 170 out of engagement with rack 208. In particular, rotation of pawl member 170 causes arm 232b to momentarily deform from its normal position.

FIG. 41 illustrates how closure of pivoting handle 14 further advances clip pusher 150. In particular, clip engaging portion 196 of clip pusher 150 advances crown portion 174a of distalmost surgical clip 148a beyond clip guide 166 and transverse protrusions 188a (not shown) and 188b of guide flanges 186a (not shown) and 186b. Further closure of pivoting handle 14 advances clip pusher 150 toward the jaw portions as shown in FIG. 42. Distalmost surgical clip 148a is driven by clip engaging portion 196 into elongated notches 102a and 102b of jaw portions 24a and 24b for subsequent deformation thereby.

As illustrated in FIG. 43, following the advancement of surgical clip 148a, rack member 208 disposed on clip pusher 150 is advanced beyond pawl member 170 and latch member 210 is configured such that shackles 216a and 216b contact pawl mount 153 on bottom plate 168. At that time, latch member 210 pivots upward against the bias of torsion spring 218, and out of engagement with protrusion 138 of channel member. As depicted in FIG. 44, clip pusher 150 returns proximally subject to the bias of return spring 204. FIG. 45 illustrates that clip engaging portion 196 of clip pusher 150 moves proximally from between jaw portions 24a and 24b. Sloping trailing edges 198a and 198b along with the resilient characteristics of clip advancement arm 194, enable clip engaging portion 196 to ride over crown portion 174b of the next surgical clip 148b, which has been advanced distally by clip follower 176. With continued reference to FIGS. 44 and 45, channel member 112 is permitted to continue advancing distally.

Figure 47:
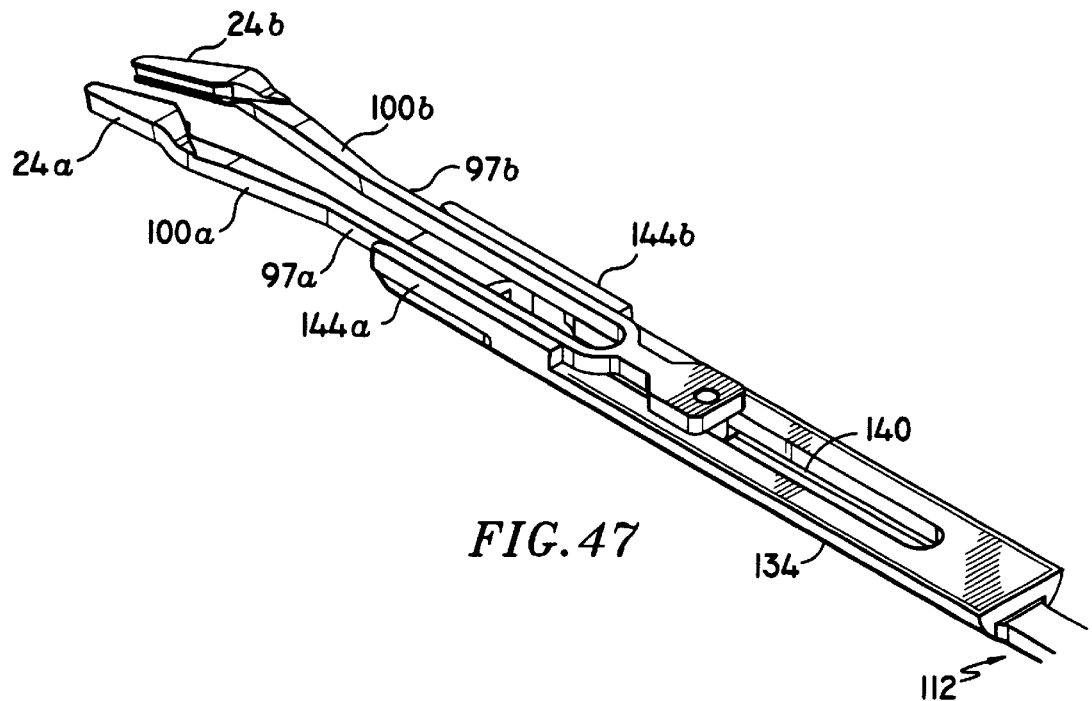
FIG. 47 is a perspective view of the jaw assembly and channel member.
Figure 48:
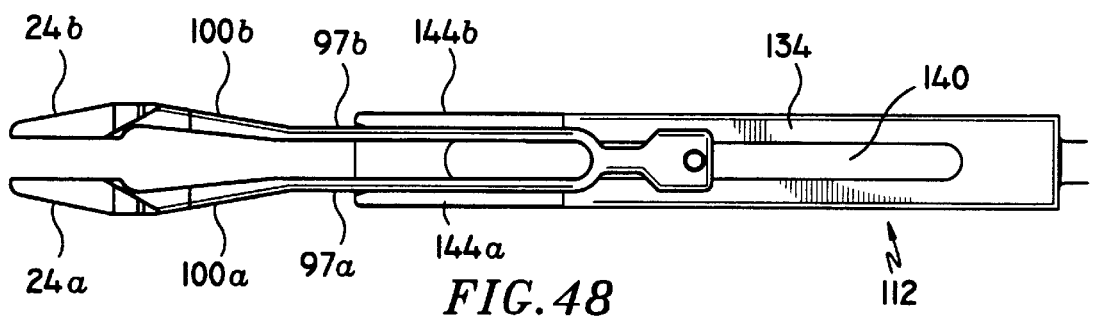
FIG. 48 is a plan view of the jaw assembly in a spaced apart configuration.
Figure 49:
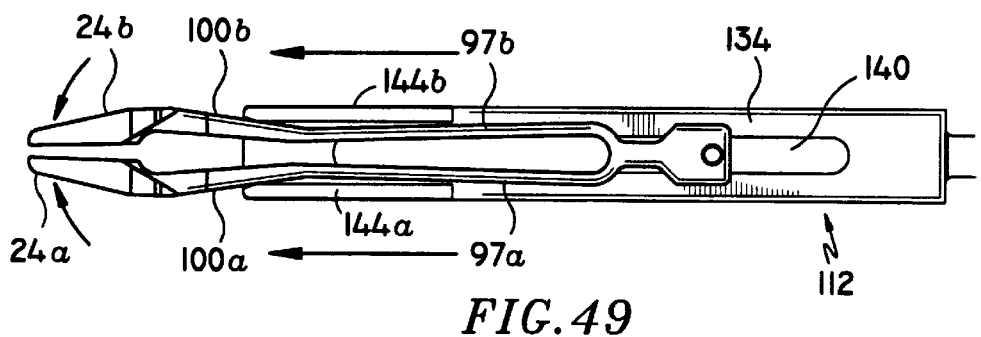
FIG. 49 is a plan view of the jaw assembly being approximated by the channel member.

Closure of jaw portions 24a and 24b, as depicted in FIG. 46, deforms surgical clip 148a held therebetween. As illustrated in FIGS. 47–49, channel member 112 is advanced distally with respect to jaw assembly 18, which is maintained stationary. Camming flanges 144a and 144b progressively approximate jaw camming surfaces 100a and 100b. Referring to FIG. 48, camming flanges 144a and 144b are disposed adjacent shank portions 97a and 97b and jaw portions 24a and 24b are in the normally spaced apart configuration for reception of a surgical clip. With further advancement of channel member 112, as in FIG. 49, camming flanges 144a and 144b engage jaw camming surfaces 100a and 100b. Due to the configuration of camming surfaces 100a and 100b, which widen towards the distal portion thereof, further displacement of channel member 112 causes jaw portions 24a and 24b to approximate, thereby deforming a surgical clip.

The above described operation of advancing a distalmost clip to the jaw portions, retracting the clip pusher proximally, and deforming the clip is repeated sequentially until the last surgical clip has been advanced from loading unit 26. After the proximalmost surgical clip has been applied, clip follower is biased distally by compression spring 178 and retained in position by clip guide 166, which acts on transverse bar 183. As described above, closure of pivoting handle 14 operatively advances clip pusher 150. Clip engaging portion 196 of clip pusher 150 engages transverse bar 183 of clip follower 176 and advances clip follower 176 beyond clip guide 166 and into elongated slots 102a and 102b of jaw portions 24a and 24b as illustrated in FIG. 50.

With reference to FIG. 51, clip follower 176 is advanced between jaw portions 24a and 24b. Clip follower 176 is constructed of an engineering plastic that is sufficiently rigid to prevent closure of jaw portions 24a and 24b when clip follower 176 is disposed therebetween. Consequently, the surgeon is provided with tactile indication of the depletion of surgical clips from loading unit 26 because channel member 112 and pivoting handle 14 are prevented from further motion. Clip follower 176 is also preferably fabricated in an bright color to provide visual indication that the loading unit 26 has been emptied of surgical clips. In addition, when the bright coloration of clip follower 176 becomes visible in viewing aperture 160, loading unit 26 only contains a few remaining surgical clips and the surgeon receives early indication of this fact.

It will be understood that various modifications may be made to the embodiments shown herein. Therefore, the above description should not be construed as limiting, but merely as exemplifications are preferred embodiments. Those skilled in the art will envision other modifications within the scope and spirit of the claims appended hereto.

What is claimed is:

1. An apparatus for application of surgical clips to body tissue, which comprises:
   a) a handle assembly;
   b) an elongated body portion extending distally from the handle assembly;
   c) a jaw assembly mounted at a distal end portion of the elongated body portion, the jaw assembly including first and second jaws movable between an open position and a closed position;
   d) an actuator slidable within the elongated body portion in response to actuation of the handle assembly, the actuator having camming structure at a distal portion thereof for moving the first and second jaws between the open position and the closed position; and
   e) a loading unit releasably mounted to the elongated body portion and storing a plurality of surgical clips therein; the loading unit including:
      i) a clip advancer having a portion engageable with the actuator and movable therewith for advancing a distalmost surgical clip; and
      ii) a ratchet assembly positioned adjacent to the clip advancer, the ratchet assembly being in operative engagement with the clip advancer to index progressive movement thereof.

2. An apparatus as recited in claim 1, wherein the actuator further includes a protrusion configured to engage a portion of the clip advancer.

3. An apparatus as recited in claim 2, wherein the portion of the clip advancer engageable with the actuator is a pivoting latch member disposed on the clip advancer.

4. An apparatus as recited in claim 1, wherein the ratchet assembly includes a rack member disposed on the clip advancer and a pawl member disposed on the loading unit.

5. An apparatus as recited in claim 4, wherein the loading unit further comprises a guide plate to direct the distalmost surgical clip to the first and second jaws during advancement by the clip advancer.

6. An apparatus as recited in claim 5, wherein the guide plate has at least one stop member configured to releasably maintain the distalmost clip within the loading unit.

7. An apparatus as recited in claim 1, wherein the handle assembly includes a stationary handle and a pivoting handle for effectuating movement of the actuator.

8. An apparatus as recited in claim 5, which further comprises a rotation knob for effectuating rotation of the elongated body portion about the longitudinal axis.

9. An apparatus for application of surgical clips to body tissue, which comprises:
 a) a handle assembly;
 b) an elongated body portion extending distally from the handle assembly;
 c) a jaw assembly mounted at a distal end portion of the elongated body portion, the jaw assembly including:
  i) first and second jaws movable between an open position and a closed position; and
  ii) a bridge portion mounted to the distal end portion of the elongated body portion adjacent the first and second jaws;
 d) an actuator slidable within the elongated body portion in response to actuation of the handle assembly, the actuator having camming structure at a distal portion thereof for moving the first and second jaws between the open position and the closed position; and
 e) a loading unit releasably mounted to the elongated body portion and storing a plurality of surgical clips therein, the loading unit including:
  i) a clip advancer having a portion engageable with the actuator and movable therewith for advancing a distalmost surgical clip; and
  ii) a ratchet assembly positioned adjacent to the clip advancer, the ratchet assembly being in operative engagement with the clip advancer to index progressive advancement thereof.

10. An apparatus as recited in claim 9, wherein the bridge portion includes a transverse member in approximation with the first and second jaw portions.

11. An apparatus as recited in claim 10, wherein the camming structure on the actuator includes a pair of flange members engageable with an outside edge of each of the first and second jaws.

12. An apparatus as recited in claim 9, wherein the actuator further includes a protrusion configured to engage a portion of the clip advancer.

13. An apparatus as recited in claim 12, wherein the portion of the clip advancer engageable with the actuator is a pivoting latch member disposed on the clip advancer.

14. An apparatus as recited in claim 9, wherein the ratchet assembly includes a rack member disposed on the clip advancer and a pawl member disposed on the loading unit.

15. An apparatus as recited in claim 9, wherein the loading unit further comprises a guide plate to direct the distalmost surgical clip to the first and second jaws during advancement by the clip advancer.

16. An apparatus as recited in claim 9, wherein the guide plate has at least one stop to releasably maintain the distalmost clip within the loading unit.

17. An apparatus for application of surgical clips to body tissue, which comprises:
 a) a handle assembly;
 b) an elongated body portion extending distally from the handle assembly;
 c) a jaw assembly mounted at a distal end portion of the elongated body portion, the jaw assembly including first and second jaws movable between an open position defining a space therebetween and a closed position;
 d) an actuator slidable within the elongated body portion in response to actuation of the handle assembly, the actuator having camming structure at a distal portion thereof for moving the first and second jaws between the open position and the closed position; and
 e) a loading unit releasably mounted to the elongated body portion, the loading unit including:
  i) a plurality of surgical clips stored within the loading unit;
  ii) a clip advancer having a portion engageable with the actuator and movable therewith for advancing a distalmost surgical clip;
  iii) a ratchet assembly positioned adjacent to the clip advancer, the ratchet assembly being in operative engagement with the clip advancer to index progressive movement thereof; and
  iv) a barrier member slidable within the loading unit and advanceable into the space between the first and second jaws to inhibit closure thereof.

18. An apparatus as recited in claim 17, wherein the barrier member is biased towards a distal end of the loading unit.

19. An apparatus as recited in claim 17, wherein the actuator further includes a protrusion configured to engage a portion of the clip advancer.

20. An apparatus as recited in claim 19, wherein the portion of the clip advancer engageable with the actuator is a pivoting latch member disposed on the clip advancer.

21. An apparatus as recited in claim 17, wherein the ratchet assembly includes a rack member disposed on the clip advancer and a pawl member disposed on the loading unit.

22. An apparatus as recited in claim 17, wherein the loading unit further comprises a guide plate to direct the distalmost surgical clip to the first and second jaws during advancement by the clip advancer.

23. An apparatus as recited in claim 17, wherein the guide plate has at least one stop member configured to releasably maintain the distalmost clip within the loading unit.

* * * * *